United States Patent
Kikugawa et al.

(10) Patent No.: US 8,435,928 B2
(45) Date of Patent: May 7, 2013

(54) HERBICIDAL COMPOSITION

(75) Inventors: Hiroshi Kikugawa, Kusatsu (JP);
Souichiro Nagayama, Kusatsu (JP);
Makiko Sano, Osaka (JP)

(73) Assignee: Ishihara Sangyo Kaisha, Ltd.,
Osaka-shi (JP)

( * ) Notice: Subject to any disclaimer, the term of this patent is extended or adjusted under 35 U.S.C. 154(b) by 262 days.

(21) Appl. No.: 12/668,725

(22) PCT Filed: Jul. 11, 2008

(86) PCT No.: PCT/JP2008/062626
§ 371 (c)(1),
(2), (4) Date: Jan. 12, 2010

(87) PCT Pub. No.: WO2009/011321
PCT Pub. Date: Jan. 22, 2009

(65) Prior Publication Data
US 2010/0197500 A1    Aug. 5, 2010

(30) Foreign Application Priority Data
Jul. 13, 2007 (JP) ................................ 2007-184482

(51) Int. Cl.
*A01N 43/40* (2006.01)
*A01N 43/56* (2006.01)
*A01N 35/00* (2006.01)

(52) U.S. Cl.
USPC ............ 504/244; 504/280; 504/282; 504/348

(58) Field of Classification Search ........................ None
See application file for complete search history.

(56) References Cited

U.S. PATENT DOCUMENTS

| | | | |
|---|---|---|---|
| 5,763,462 A | 6/1998 | Iwasaki | |
| 6,376,429 B1 | 4/2002 | Van Almsick et al. | |
| 2002/0016345 A1 | 2/2002 | Edmunds et al. | |
| 2005/0202975 A1 | 9/2005 | Stock et al. | |
| 2009/0170702 A1 | 7/2009 | Yoshii et al. | |
| 2010/0041557 A1* | 2/2010 | Hupe et al. ........... | 504/348 |
| 2010/0099563 A1* | 4/2010 | Shimoharada et al. ...... | 504/134 |
| 2011/0166023 A1* | 7/2011 | Nettleton-Hammond et al. ............ | 504/133 |

FOREIGN PATENT DOCUMENTS

| | | |
|---|---|---|
| CN | 1318055 A | 10/2001 |
| CN | 1658756 A | 2/2005 |
| CN | 1658756 A | 8/2005 |
| JP | 55 31013 | 3/1980 |
| JP | 63 253005 | 10/1988 |
| JP | 11 236376 | 8/1999 |
| JP | 2001 89307 | 4/2001 |
| JP | 2001 122848 | 5/2001 |
| JP | 2002 524554 | 8/2002 |
| JP | 2005 145901 | 6/2005 |
| JP | 2005 529174 | 9/2005 |
| JP | 2008 81487 | 4/2008 |
| JP | 2008 156338 | 7/2008 |
| WO | 00 53014 | 9/2000 |
| WO | WO 01/14303 A1 | 3/2001 |
| WO | 01 94339 | 12/2001 |
| WO | WO 2006097322 * | 9/2006 |
| WO | 2007 069771 | 6/2007 |
| WO | 2008 065907 | 6/2008 |
| WO | 2008 078811 | 7/2008 |

OTHER PUBLICATIONS

U.S. Appl. No. 13/133,993, filed Jun. 10, 2011, Kikugawa, et al.
U.S. Appl. No. 12/993,760, filed Nov. 19, 2010, Tsukamoto, et al.
Chinese Office Action issued Jun. 26, 2012, in China patent Application No. 200880024096.8 (English Translation Only).
Chinese Office Action issued Jun. 26, 2012, in China patent Application No. 200880024096.8.
Supplementary European Search Report and Search Opinion dated Dec. 13, 2012 as received in the corresponding EP Patent Application No. 08791107.9-2103/2172104.

* cited by examiner

*Primary Examiner* — Alton Pryor
(74) *Attorney, Agent, or Firm* — Oblon, Spivak, McClelland, Maier & Neustadt, L.L.P.

(57) ABSTRACT

To provide a herbicidal composition and a method for its application, whereby the effect of a herbicidally active ingredient is improved to reduce the environmental load on a site where the herbicide is applied or the periphery thereof, more than ever, and its dose can be reduced.

A herbicidal composition comprising (1) a compound represented by the formula (I) or its salt:

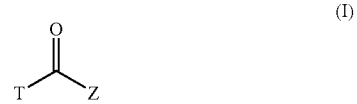

where T and Z are as defined in the specification, and (2) a polyoxyalkylene alkyl ether phosphate or its salt. A method for controlling undesired plants or inhibiting their growth, by applying the herbicidal composition.

14 Claims, No Drawings

HERBICIDAL COMPOSITION

CROSS-REFERENCE TO RELATED APPLICATIONS

This application is a National Stage of PCT/JP08/062,626 filed Jul. 11, 2008 and claims the benefit of JP 2007-184482 filed Jul. 13, 2007.

TECHNICAL FIELD

The present invention relates to a herbicidal composition which improves the herbicidal effect of a compound represented by the following formula (I) or its salt by use of a polyoxyalkylene alkyl ether phosphate or its salt.

BACKGROUND ART

Heretofore, in cultivation of crop plants in cropland, it has been desired to control weeds which inhibit the growth or the harvest of crop plants. Further, in non-cropland also, it is beneficial for utilization of the non-cropland to effectively control weeds. Thus, control of weeds is necessary in each of cropland and non-cropland, and various herbicides have been used. However, in recent years, there is a movement to reduce the dosage of a herbicidally active ingredient as far as possible, so as to reduce the environment load at a site where the herbicide is applied or the periphery thereof. For example, it is known to blend a nonionic surfactant to a spray solution thereby to improve the herbicidal effect and to reduce the dosage of the herbicide. As a general purpose product, an alkyl aryl polyglycol ether type surfactant (tradename: CITOWETT, manufactured by BASF France) or a silicon type surfactant (tradename: SILWETT L-77, polyalkylene oxide modified heptamethyl-trisiloxane, manufactured by Helena Chemical Company) may, for example, be mentioned.

The compound represented by the following formula (I) or its salt is disclosed in Patent Documents 1 to 4, but it is not known that its herbicidal effect is remarkably improved by a polyoxyalkylene alkyl ether phosphate or its salt.

Patent Document 5 discloses a herbicidal mixture comprising a 3-hetero ring-substituted benzoyl derivative or its salt, and an adjuvant containing a $C_{1-5}$ alkyl ester of a $C_{5-22}$ alkanoic acid, a $C_{10-20}$ carboxylic acid, a partial phosphate or partial sulfate of a monohydroxy-functional polyalkyl ether and, as the case requires, an alkylpolyoxyalkylene polyether.

Patent Document 1: WO2007/069771
Patent Document 2: U.S. Pat. No. 6,376,429
Patent Document 3: WO2008/068907
Patent Document 4: WO2001/094339
Patent Document 5: WO2000/53014

DISCLOSURE OF THE INVENTION

Object to be Accomplished by the Invention

It has been desired to improve the effect of a herbicidally active ingredient and to reduce the dosage as far as possible, in order to reduce the environmental load on a site where the herbicide is applied or the periphery thereof, more than ever.

Means to Accomplish the Object

The present inventors have conducted extensive studies to accomplish the above object and as a result, have found that the herbicidal effect of the compound represented by the following formula (I) or its salt can be remarkably improved by using a specific compound, and have accomplished the present invention.

That is, the present invention relates to a herbicidal composition comprising (1) a compound represented by the formula (I) or its salt:

(I)

wherein T is $T^1$:

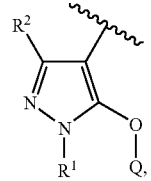

$T^2$:

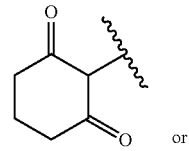

or $T^3$:

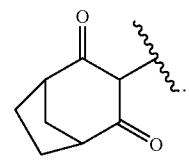

and Z is $Z^1$:

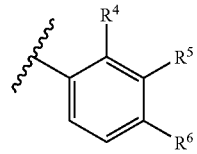

or $Z^2$:

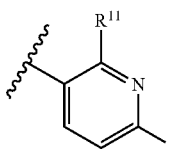

Q is —C(O)SR$^3$, hydrogen or A-O—C(O)OR$^{10}$, R$^1$ is alkyl or cycloalkyl, R$^2$ is hydrogen or alkyl, R$^3$ is alkyl; cycloalkyl; haloalkyl; alkoxyalkyl; alkoxycarbonylalkyl; alkenyl; or arylalkyl which may be substituted by R$^8$, R$^4$ is alkyl; haloalkyl; alkoxy; halogen; nitro; cyano; alkylthio; alkylsulfinyl; or alkylsulfonyl, R$^5$ is hydrogen; alkyl; alkenyl; alkynyl; halogen; cyano; cyanoalkyl; cyanoalkenyl; haloalkyl; alkoxyalkyl; haloalkoxyalkyl; amino(thiocarbonyl)alkyl which may be substituted by at least one substituent selected from the group consisting of alkyl, cyano, cyanoalkyl, (alkylthio)carbonylalkyl, alkyl(thiocarbonyl)alkyl, —C(O)OR$^7$ and —C(O)SR$^7$; thiocyanatoalkyl; alkoxy; alkenyloxy; alkynyloxy; haloalkoxy; alkoxyalkoxy; haloalkoxyalkoxy; alkoxyhaloalkoxy; haloalkoxyhaloalkoxy; alkoxyalkoxyalkyl; alkylthio; alkoxyalkylthio; haloalkoxyalkylthio; alkoxyhaloalkylthio; haloalkoxyhaloalkylthio; alkylthioalkylthio; haloalkylthioalkylthio; alkylthiohaloalkylthio; haloalkylthiohaloalkylthio; alkylthioalkoxy; alkylsulfonyl; alkylsulfonylalkyl; alkoxycarbonylalkyl; alkoxycarbonylalkoxy; heterocyclic alkyl; heterocyclic oxy; heterocyclic alkoxy; heterocyclic alkoxyalkyl; heterocyclic oxyalkyl; cycloalkyloxy; —OC(O)SR$^7$; —OC(O)OR$^7$; —C(O)OR$^7$; —C(O)SR$^7$; —C(S)OR$^7$; —C(S)SR$^7$; or aminoalkyl which may be substituted by at least one substituent selected from the group consisting of alkyl, cyano, cyanoalkyl, (alkylthio)carbonylalkyl, alkyl(thiocarbonyl)alkyl, —C(O)OR$^7$ and —C(O)SR$^7$, R$^6$ is haloalkyl; halogen; nitro; cyano; alkylthio; alkylsulfinyl; or alkylsulfonyl, R$^7$ is alkyl; haloalkyl; alkoxyalkyl; alkenyl; haloalkenyl; alkynyl; or arylalkyl which may be substituted by R$^9$; each of R$^8$ and R$^9$ which are independent of each other, is halogen; alkyl; or alkoxy; R$^{10}$ is alkyl, A is alkylene substituted by at least one alkyl, R$^{11}$ is alkoxyalkoxyalkyl, and R$^{12}$ is haloalkyl, provided that when T is T$^1$ or T$^2$, Z is Z$^1$, when T is T$^3$, Z is Z$^2$, when T is T$^1$ and R$^5$ is hydrogen, Q is not hydrogen, and when T is T$^2$, R$^5$ is not hydrogen, and (2) a polyoxyalkylene alkyl ether phosphate or its salt.

Effects of the Invention

According to the present invention, the herbicidal effect of a compound represented by the above formula (I) (hereinafter referred to as a compound of the formula (I)) or its salt is effectively brought about and improved by a polyoxyalkylene alkyl ether phosphate (hereinafter referred to as a POA alkyl ether phosphate) or its salt. Further, the dosage of the herbicide can be reduced by the POA alkyl ether phosphate or its salt, whereby the environmental load on a site where the herbicide is applied or the periphery thereof can be remarkably reduced and further, the reduction in the dosage of the herbicide contributes to remarkable reduction in the cost required for storage or transportation.

BEST MODE FOR CARRYING OUT THE INVENTION

The herbicidal composition of the present invention comprises a compound of the formula (I) or its salt and a POA alkyl ether phosphate or its salt. For example, the present invention is applied in such a manner that (a) a compound of the formula (I) or its salt is formulated by using various additives, the formulation is diluted with e.g. water together with a POA alkyl ether phosphate or its salt, and the diluted liquid is applied to undesired plants or to a place where they grow, or (b) a compound of the formula (I) or so its salt, and a POA alkyl ether phosphate or its salt, are formulated together with various additives, and the resulting formulation diluted with e.g. water or as it is without dilution, is applied to undesired plants or to a place where they grow.

The salt of the compound of the formula (I) may be any salt so long as it is agriculturally acceptable, and it may, for example, be an alkali metal salt such as a sodium salt or a potassium salt; an alkaline earth metal salt such as a magnesium salt or a calcium salt; an amine salt such as a dimethylamine salt or a triethylamine salt; an inorganic acid salt such as a hydrochloride, a perchlorate, a sulfate or a nitrate; or an organic acid salt such as an acetate or a methanesulfonate.

In a case where the compound of the formula (I) has various structural isomers such as optical isomers, geometric isomers or keto-enol tautomers, such isomers are, of course, included in the compound of the formula (I).

The POA alkyl ether phosphate in the present invention may, for example, be a mono-POA alkyl ether phosphate, a di-POA alkyl ether phosphate or a tri-POA alkyl ether phosphate, having 1 to 3 POA alkyl ether moieties bonded to a phosphorus atom, and in a case where a plurality of POA alkyl ether moieties are bonded to a phosphorus atom, they may be the same or the different. In the present invention, the above-described phosphates may optionally be mixed.

The long chain alkyl moiety located at a terminal or at a position interposed between POA moieties of the POA alkyl ether phosphate in the present invention may be either linear or blanched, and it preferably has, for example, from about 8 to about 20 carbon atoms. Specific examples thereof include octyl, nonyl, decyl, undecyl, dodecyl, tridecyl, tetradecyl, pentadecyl, hexadecyl, heptadecyl, octadecyl, nonadecyl and eicosyl.

In the present invention, the number of addition of POA moiety in the POA alkyl ether phosphate is from about 1 to about 50, preferably from about 1 to about 20. Further, the alkylene oxide moiety in the POA alkyl ether phosphate may be linear or branched, and it preferably has, for example, from about 2 to about 3 carbon atoms. Specific examples thereof include ethylene oxide, propylene oxide and —CH(CH$_3$)CH$_2$O—. Their copolymers and block copolymers may also be mentioned. The position of substitution of the alkylene oxide moiety is not particularly limited.

In the present invention, as the salt of the POA alkyl ether phosphate, various salts may be mentioned, such as a salt with an alkali metal such as sodium or potassium; a salt with an alkaline earth metal such as magnesium or calcium; a salt with NH$_4^+$; and an amine salt such as a salt with a monoethanolamine, a salt with a diethanolamine, a salt with a triethanolamine, a salt with a trimethylamine, a salt with a triethylamine, a salt with a tributylamine, a salt with a diisopropylethylamine or a salt with morpholine.

In the present invention, in a case where the POA alkyl ether phosphate is used in the form of a salt, the POA alkyl ether phosphate may be added to a spray solution or a formulation, followed by neutralization with a base to form a salt in a spray tank or during formulation. Otherwise, the POA alkyl ether phosphate as it is or in a solution state such as an aqueous solution, is preliminarily neutralized with a base to form a salt, which is then added to a spray solution or a formulation. In either case, the base to be used may be added as it is or in a solution state such as an aqueous solution.

The base to be used for the neutralization may be either an inorganic base or an organic base. The inorganic base may, for example, be an alkali metal carbonate such as sodium carbonate or potassium carbonate; an alkali metal hydrogencarbonate such as sodium hydrogencarbonate or potassium hydrogencarbonate; an alkaline earth metal carbonate such as magnesium carbonate, calcium carbonate or barium carbonate; an alkali metal hydroxide such as lithium hydroxide, sodium hydroxide or potassium hydroxide; or an alkaline earth metal hydroxide such as magnesium hydroxide, calcium hydroxide or barium hydroxide. The organic base may, for example, be an amine such as ammonia, monoethanolamine, diethanolamine, triethanolamine, trimethylamine, triethylamine, tributylamine, diisopropylethylamine or morpholine. The base may be used alone or as a mixture of two or more of them.

As examples of the chemical structure of the POA alkyl ether phosphate in the present invention, compounds of the following formulae (II), (III) and (IV) may be mentioned. However, the present invention is by no means restricted thereto.

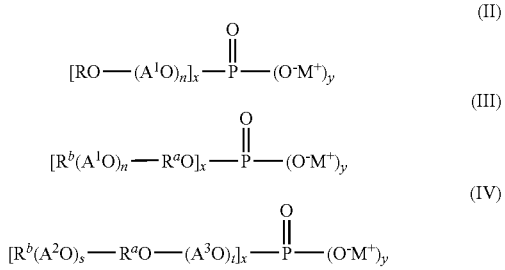

In the above formulae, each of R and $R^b$ is alkyl, each of $R^a$, $A^1$, $A^2$ and $A^3$ is alkylene, $M^+$ is a hydrogen ion, a metal ion, ammonium or an organic ammonium, each of n, s and t is an integer of at least 1, and x and y satisfy x+y=3, x is an integer of 1, 2 or 3 and y is an integer of 0, 1 or 2. When x is at least 2, R's, $R^a$'s, $R^b$'s, $A^1$'s, $A^2$'s, $A^3$'s and n's in the respective $[RO(A^1O)_n]$, $[R^b(A^1O)_nR^aO]$ and $[R^b(A^2O)_sR^aO(A^3O)_t]$ may be the same or different. When y is 2, $M^+$'s may be the same or different. In the formula (IV), $A^2$ and $A^3$ may be the same or different.

The POA alkyl ether phosphate or its salt in the present invention is also known, for example, as a phosphate ester of an alkoxylated alcohol or its salt, a phosphated alcohol alkoxylate or its salt, or a (polyoxyalkylene alcohol) phosphate or its salt. They are all included in the POA alkyl ether phosphate or its salt used in the present invention, and the present invention is not limited thereto.

In the present invention, a surfactant containing a POA alkyl ether phosphate or its salt may be used, and the following may be mentioned as specific examples thereof.

NIKKOL DLP-10, NIKKOL DOP-8NV, NIKKOL DDP-2, NIKKOL DDP-4, NIKKOL DDP-6, NIKKOL DDP-8, NIKKOL DDP-10, NIKKOL TCP-4, NIKKOL TCP-5, NIKKOL TDP-2, NIKKOL TDP-6, NIKKOL TDP-8, NIKKOL TDP-10, etc., tradenames, manufactured by NIKKO CHEMICALS CO., LTD.

PLYSURF A212C, PLYSURF A215C, PLYSURF A208B, PLYSURF A219B, etc., tradenames, manufactured by DAI-ICHI KOGYO SEIYAKU CO., LTD.

PHOSPHANOL ED-200, PHOSPHANOL RA-600, PHOSPHANOL ML-220, PHOSPHANOL ML-240, PHOSPHANOL RD-510Y, PHOSPHANOL RS-410, PHOSPHANOL RS-610, PHOSPHANOL RS-710, PHOSPHANOL RL-210, PHOSPHANOL RL-310, PHOSPHANOL RB-410, PHOSPHANOL RS-610NA, PHOSPHANOL SC-6103, PHOSPHANOL RS-710M, PHOSPHANOL GB-520, PHOSPHANOL RD-720, etc., tradenames, manufactured by TOHO Chemical Industry Co., Ltd.

ADEKA COL PS-440E, ADEKA COL PS-509E, ADEKA COL PS-807, ADEKA COL PS-810, ADEKA COL PS-984, etc., tradenames, manufactured by ADEKA CORPORATION.

PHOSPHOLAN 5AP, PHOSPHOLAN PS-131, PHOSPHOLAN PS-220, PHOSPHOLAN PS-222, PHOSPHOLAN PS-236, PHOSPHOLAN PS-331, PHOSPHOLAN PS-810, PHOSPHOLAN PS-900, etc., tradenames, manufactured by AKZO NOVEL.

AGNIQUE PE23-5, AGNIQUE PE25-5, AGNIQUE PE25-5K, AGNIQUE PE28-5N, Crafol AP67, etc., tradenames, manufactured by Cognis Deutschland GmbH Co. & KG.

In the present invention, an oil such as a vegetable oil, a fatty acid ester or a hydrocarbon solvent may be used as a coadjuvant, as the case requires, in order to more significantly improve the herbicidal effect of the compound of the formula (I) or its salt, to expand the range of plants against which the herbicidal effect is exhibited, or to expand the timing for the application of the herbicide. As such an oil, one type or more may optionally be used.

The vegetable oil may, for example, be olive oil, kapok oil, castor oil, palm oil, camellia oil, coconut oil, sesame oil, corn oil, rice bran oil, peanut oil, cotton oil, soybean oil, rapeseed oil, linseed oil or tung oil.

The fatty acid ester may be one derived from a vegetable oil or an animal oil as the starting material or may be one chemically synthesized from a petroleum oil. Further, the alkyl moiety of such a fatty acid may be saturated or unsaturated and may be straight chained or branched. A common product derived from a vegetable oil as the starting material may, for example, be methylated seed oil (MSO).

The hydrocarbon solvent may, for example, be xylene, an alkylbenzene, an alkylnaphthalene, other high boiling point aromatic hydrocarbons, normal paraffin (saturated linear hydrocarbon), isoparaffin (saturated branched hydrocarbon), naphthene (saturated cycloalkane) or a mixture thereof.

The following ones may, for example, be mentioned as specific examples of a product containing the aromatic hydrocarbon:

Solvesso 100, Solvesso 150, Solvesso 200, etc., tradenames, manufactured by Exxon Mobil Chemical Company.

Nisseki Hisol SAS296, Nisseki Hisol SAS LH, etc., tradenames, manufactured by Nippon Oil Corporation.

Shellsol A100, Shellsol A150, etc., tradenames, manufactured by Shell Chemicals Japan Ltd.

The following ones may, for example, be mentioned as specific examples of a product containing normal paraffin or isoparaffin.

Normal Paraffin SL, Normal Paraffin L. Normal Paraffin M, Normal Paraffin H, Sunsol IP600, etc., tradenames, manufactured by Nippon Oil Corporation.

Shellsol S, Shellsol TG, Shellsol TK, Shellsol™, etc., tradenames, manufactured by Shell Chemicals Japan Ltd.

The following ones may, for example, be mentioned as specific examples of a product containing naphthene:

Naphtesol 160, Naphtesol 200, Naphtesol 220, Naphtesol MS-20P, etc., tradenames, manufactured by Nippon Oil Corporation.

Shellsol D40, Shellsol D70, etc., tradenames, manufactured by Shell Chemicals Japan Ltd.

In the present invention, in a case where the above oil is to be used, an emulsifying agent i.e. a surfactant having an emulsifying effect other than the POA alkyl ether phosphate or its salt, may be used as the case requires. By incorporating such an emulsifying agent, the water dispersibility of the above oil can be improved, such being advantageous in a case where a herbicidal composition containing the compound of the formula (I) or its salt is to be applied as diluted with water. This is one of preferred embodiments in the present invention. Further, the emulsifying agent may be used in a form as preliminarily mixed with the POA alkyl ether phosphate or its salt or with the above oil, or may be used by mixing it at the time of preparing a spray solution.

The above emulsifying agent, may, for example, be the following nonionic surfactant or anionic surfactant. Such surfactants may be used alone or in optional combination as a mixture.

The nonionic surfactant may, for example, be a polyoxyalkylene alkyl ether, a polyoxyalkylene alkyl ether, a polyoxyalkylene alkyl aryl ether, a polyoxyalkylene styryl phenyl ether, a polyoxyalkylene alkyl ester, a polyoxyalkylene sorbitan alkyl ester, a polyoxyalkylene sorbitol alkyl ester, a polyoxyalkylene sorbitan fatty acid ester, a polyoxyalkylene sorbitol fatty acid ester, a polyoxyalkylene phenyl ether polymer, a polyoxyalkylene alkylene aryl phenyl ether, a polyoxyalkylene aryl phenyl ether, a polyoxyalkylene alkylene glycol, a polyoxyalkylene polyoxypropylene block polymer, a polyoxyalkylene hydrogenated castor oil or a polyoxyalkylene castor oil.

The anionic surfactant may, for example, be a polycarboxylic acid type surfactant, a lignin sulfonate, an alkyl aryl sulfonate, a dialkyl sulfosuccinate, a polyoxyalkylene alkyl aryl ether sulfate, an alkylnaphthalene sulfonate, a polyoxyalkylene styryl phenyl ether sulfate, a polyoxyalkylene styrene-modified phenyl ether phosphate, an alkylbenzene sulfonate (such as sodium dodecylbenzene sulfonate) or an alkyl sulfate (such as sodium lauryl sulfate).

The herbicidal composition of the present invention may be either in a form such that the herbicidal composition containing the compound of the formula (I) or its salt, and the POA alkyl ether phosphate or its salt, or a surfactant containing it, are mixed, for example, at the time of application, or in a form such that they are preliminarily formulated. The same applies to a case where an oil or an emulsifying agent as a coadjuvant is used. Various additives may be used if desired, when the compound of the formula (I) or its salt and the POA alkyl ether phosphate or its salt are formulated, or when the above oil is further added to the above compounds and formulated. The additives to be used are not particularly limited so long as they can be used in this technical field, and examples thereof include a surfactant other than the POA alkyl ether phosphate, a carrier, a binder, a vegetable oil, a mineral oil, an anti-settling agent, a thickener, an antifoaming agent and an antifreezing agent. Formulation may be carried out in accordance with a conventional method in this technical field.

In the present invention, a herbicidal compound other than the compound of the formula (I) or its salt may be mixed or used in combination if desired, whereby more excellent effects or activity may be exhibited in some cases. For example, it may sometimes be possible to improve e.g. the range of the weeds to be controlled, the timing for the application of the herbicide or the herbicidal activities. The compound of the formula (I) or its salt and another herbicidal compound may be individually prepared and mixed at the time of application, or they may be formulated together and applied. Such another herbicidal compound may suitably be selected from the following compound groups (1) to (11) (common names including ones under application for approval by ISO). Even when not specifically mentioned here, in a case where such compounds have salts, alkyl esters, structural isomers such as optical isomers etc., they are, of course, all included.

(1) Those which are believed to exhibit herbicidal effects by disturbing hormone activities of plants, such as a phenoxy type such as 2,4-D, 2,4-D-butotyl, 2,4-D-butyl, 2,4-D-dimethylammonimum, 2,4-D-diolamine, 2,4-D-ethyl, 2,4-D-2-ethylhexyl, 2,4-D-isobutyl, 2,4-D-isoctyl, 2,4-D-isopropyl, 2,4-D-isopropylammonium, 2,4-D-sodium, 2,4-D-isopropanolammonium, 2,4-D-trolamine, 2,4-DB, 2,4-DB-butyl, 2,4-DB-dimethylammonium, 2,4-DB-isoctyl, 2,4-DB-potassium, 2,4-DB-sodium, dichlorprop, dichlorprop-butotyl, dichlorprop-dimethylammonium, dichlorprop-isoctyl, dichlorprop-potassium, dichlorprop-P, dichlorprop-P-dimethylammonium, dichlorprop-P-potassium, dichlorprop-P-sodium, MCPA, MCPA-butotyl, MCPA-dimethylammonium, MCPA-2-ethylhexyl, MCPA-potassium, MCPA-sodium, MCPA-thioethyl, MCPB, MCPB-ethyl, MCPB-sodium, mecoprop, mecoprop-butotyl, mecoprop-sodium, mecoprop-P, mecoprop-P-butotyl, mecoprop-P-dimethylammonium, mecoprop-P-2-ethylhexyl, mecoprop-P-potassium, naproanilide or clomeprop; an aromatic carboxylic acid type such as 2,3,6-TBA, dicamba, dicamba-butotyl, dicamba-diglycolamine, dicamba-dimethylammonium, dicamba-diolamine, dicamba-isopropylammonium, dicamba-potassium, dicamba-sodium, dichlobenil, picloram, picloram-dimethylammonium, picloram-isoctyl, picloram-potassium, picloram-triisopropanolammonium, picloram-triisopropylammonium, picloram-trolamine, triclopyr, triclopyr-butotyl, triclopyr-triethylammonium, clopyralid, clopyralid-olamine, clopyralid-potassium, clopyralid-triisopropanolammonium or aminopyralid; and others such as naptalam, naptalam-sodium, benazolin, benazolin-ethyl, quinclorac, quinmerac, diflufenzopyr, diflufenzopyr-sodium, fluoroxypyr, fluoroxypyr-2-butoxy-1-methylethyl, fluoroxypyr-meptyl, chlorflurenol or chlorflurenol-methyl.

(2) Those which are believed to exhibit herbicidal effects by inhibiting photosynthesis of plants, such as a urea type such as chlorotoluron, diuron, fluometuron, linuron, isoproturon, metobenzuron, tebuthiuron, dimefuron, isouron, karbutilate, methabenzthiazuron, metoxuron, monolinuron, neburon, siduron, terbumeton or trietazine; a triazine type such as simazine, atrazine, atratone, simetryn, prometryn, dimethametryn, hexazinone, metribuzin, terbuthylazine, cyanazine, ametryn, cybutryne, triaziflam, terbutryn, propazine, metamitron or prometon; a uracil type such as bromacil, bromacyl-lithium, lenacil or terbacil; an anilide type such as propanil or cypromid; a carbamate type such as swep, desmedipham or phenmedipham; a hydroxybenzonitrile type such as bromoxynil, bromoxynil-octanoate, bromoxynil-heptanoate, ioxynil, ioxynil-octanoate, ioxynil-potassium or ioxynil-sodium; and others such as pyridate, bentazone, bentazone-sodium, amicarbazone, methazole or pentanochlor.

(3) Quaternary ammonium salt type such as paraquat or diquat, which is believed to be converted to free radicals by itself to form active oxygen in the plant body and shows rapid herbicidal efficacy.

(4) Those which are believed to exhibit herbicidal effects by inhibiting chlorophyll biosynthesis of plants and abnormally accumulating a photosensitizing peroxide substance in the plant body, such as a diphenylether type such as nitrofen, chlomethoxyfen, bifenox, acifluorfen, acifluorfen-sodium, fomesafen, fomesafen-sodium, oxyfluorfen, lactofen, aclonifen, ethoxyfen-ethyl (HC-252), fluoroglycofen-ethyl or fluoroglycofen; a cyclic imide type such as chlorphthalim, flumioxazin, flumiclorac, flumiclorac-pentyl, cinidon-ethyl or fluthiacet-methyl; and others such as oxadiargyl, oxadiazon, sulfentrazone, carfentrazone-ethyl, thidiazimin, pentoxazone, azafenidin, isopropazole, pyraflufen-ethyl, benzfendizone, butafenacil, saflufenacil, flupoxam, fluazolate, profluazol, pyraclonil, flufenpyr-ethyl or bencarbazone.

(5) Those which are believed to exhibit herbicidal effects characterized by bleaching activities by inhibiting chromogenesis of plants such as carotenoids, such as a pyridazinone type such as norflurazon, chloridazon or metflurazon; a pyrazole type such as pyrazolynate, pyrazoxyfen, benzofenap, topramezone (BAS-670H) or pyrasulfotole; and others such as amitrole, fluridone, flurtamone, diflufenican, methoxyphenone, clomazone, sulcotrione, mesotrione, tembotrione, tefuryltrione (AVH-301), isoxaflutole, difenzoquat, difenzoquat-metilsulfate, isoxachlortole, benzobicyclon, picolinafen or beflubutamid.

(6) Those which exhibit strong herbicidal effects specifically to gramineous plants, such as an aryloxyphenoxypropionic acid type such as diclofop-methyl, diclofop, pyriphenop-sodium, fluazifop-butyl, fluazifop, fluazifop-P, fluazifop-P-butyl, haloxyfop-methyl, haloxyfop, haloxyfop-etotyl, haloxyfop-P, haloxyfop-P-methyl, quizalofop-ethyl, quizalofop-P, quizalofop-P-ethyl, quizalofop-P-tefuryl, cyhalofop-butyl, fenoxaprop-ethyl, fenoxaprop-P, fenoxaprop-P-ethyl, metamifop-propyl, metamifop, clodinafop-propargyl, clodinafop or propaquizafop; a cyclohexanedione type such as alloxydim-sodium, alloxydim, clethodim, sethoxydim, tralkoxydim, butroxydim, tepraloxydim, profoxydim or cycloxydim; and others such as flamprop-M-methyl, flamprop-M or flamprop-M-isopropyl.

(7) Those which are believed to exhibit herbicidal effects by inhibiting an amino acid biosynthesis of plants, such as a sulfonylurea type such as chlorimuron-ethyl, chlorimuron, sulfometuron-methyl, sulfometuron, primisulfuron-methyl, primisulfuron, bensulfuron-methyl, bensulfuron, chlorsulfuron, metsulfuron-methyl, metsulfuron, cinosulfuron, pyrazosulfuron-ethyl, pyrazosulfuron, azimsulfuron, flazasulfuron, rimsulfuron, nicosulfuron, imazosulfuron, cyclosulfamuron, prosulfuron, flupyrsulfuron-methyl-sodium, flupyrsulfuron, triflusulfuron-methyl, triflusulfuron, halosulfuron-methyl, halosulfuron, thifensulfuron-methyl, thifensulfuron, ethoxysulfuron, oxasulfuron, ethametsulfuron, ethametsulfuron-methyl, iodosulfuron, iodosulfuron-methyl-sodium, sulfosulfuron, triasulfuron, tribenuron-methyl, tribenuron, tritosulfuron, foramsulfuron, trifloxysulfuron, trifloxysulfuron-sodium, mesosulfuron-methyl, mesosulfuron, orthosulfamuron, flucetosulfuron, amidosulfuron, TH-547 or a compound disclosed in WO2005092104; a triazolopyrimidinesulfonamide type such as flumetsulam, metosulam, diclosulam, cloransulam-methyl, florasulam or penoxsulam; an imidazolinone type such as imazapyr, imazapyr-isopropylammonium, imazethapyr, imazethapyr-ammonium, imazaquin, imazaquin-ammonium, imazamox, imazamox-ammonium, imazamethabenz, imazamethabenz-methyl or imazapic; a pyrimidinylsalicylic acid type such as pyrithiobac-sodium, bispyribac-sodium, pyriminobac-methyl, pyribenzoxim, pyriftalid or pyrimisulfan (KUH-021); a sulfonylaminocarbonyltriazolinone type such as flucarbazone, flucarbazone-sodium, propoxycarbazone-sodium or propoxycarbazone; and others such as glyphosate, glyphosate-sodium, glyphosate-potassium, glyphosate-ammonium, glyphosate-diammonium, glyphosate-isopropylammonium, glyphosate-trimesium, glyphosate-sesquisodium, glufosinate, glufosinate-ammonium, bilanafos, bilanafos-sodium or cinmethylin.

(8) Those which are believed to exhibit herbicidal effects by inhibiting cell mitoses of plants, such as a dinitroaniline type such as trifluralin, oryzalin, nitralin, pendimethalin, ethalfluralin, benfluralin, prodiamine, butralin or dinitramine; an amide type such as bensulide, napropamide, propyzamide or pronamide; an organic phosphorus type such as amiprofos-methyl, butamifos, anilofos or piperophos; a phenyl carbamate type such as propham, chlorpropham, barban or carbetamide; a cumylamine type such as daimuron, cumyluron, bromobutide or methyldymron; and others such as asulam, asulam-sodium, dithiopyr, thiazopyr, chlorthal-dimethyl, chlorthal or diphenamid.

(9) Those which are believed to exhibit herbicidal effects by inhibiting protein biosynthesis or lipid biosynthesis of plants, such as a chloroacetamide type such as alachlor, metazachlor, butachlor, pretilachlor, metolachlor, S-metolachlor, thenylchlor, pethoxamid, acetochlor, propachlor, dimethenamid, dimethenamid-P, propisochloror dimethachlor; a thiocarbamate type such as molinate, dimepiperate, pyributicarb, EPTC, butylate, vemolate, pebulate, cycloate, prosulfocarb, esprocarb, thiobencarb, diallate, tri-allate or orbencarb; and others such as etobenzanid, mefenacet, flufenacet, tridiphane, cafenstrole, fentrazamide, oxaziclomefone, indanofan, benfuresate, pyroxasulfone (KIH-485), dalapon, dalapon-sodium, TCA-sodium or trichloroacetic acid.

(10) MSMA, DSMA, CMA, endothall, endothall-dipotassium, endothall-sodium, endothall-mono(N,N-dimethylalkylammonium), ethofumesate, sodium chlorate, pelargonic acid (nonanoic acid), fosamine, fosamine-ammonium, pinoxaden, HOK-201, aclolein, ammonium sulfamate, borax, chloroacetic acid, sodium chloroacete, cyanamide, methylarsonic acid, dimethylarsinic acid, sodium dimethylarsinate, dinoterb, dinoterb-ammonium, dinoterb-diolamine, dinoterb-acetate, DNOC, ferrous sulfate, flupropanate, flupropanate-sodium, isoxaben, mefluidide, mefluidide-diolamine, metam, metam-ammonium, metam-potassium, metam-sodium, methyl isothiocyanate, pentachlorophenol, sodium pentachlorophenoxide, pentachlorophenol laurate, quinoclamine, sulfuric acid, urea sulfate, etc.

(11) Those which are believed to exhibit herbicidal effects by being parasitic on plants, such as *Xanthomonas campestris, Epicoccosirus nematosorus, Epicoccosirus nematosperus, Exserohilum monoseras* or *Drechsrela monoceras*.

The herbicidal composition of the present invention is capable of controlling a wide range of undesired weeds, such as gramineae such as bamyardgrass (*Echinochloa crus-qalli* L., *Echinochloa oryzicola* vasing.), crabgrass (*Digitaria sanguinalis* L., *Digitaria ischaemum* Muhl., *Digitaria adscendens* Henr., *Digitaria microbachne* Henr., *Digitaria horizontalis* Willd.), green foxtail (*Setaria viridis* L.), giant foxtail (*Setaria faberi* Herrm.), yellow foxtail (*Setaria lutescens* Hubb.), goosegrass (*Eleusine indica* L.), wild oat (*Avena fatua* L.), johnsongrass (*Sorghum halepense* L.), quackgrass (*Aqropyron repens* L.), alexandergrass (*Brachiaria plantaqinea*), guineagrass (*Panicum maximum* Jacq.), paragrass (*Panicum purpurascens*), sprangletop (*Leptochloa chinensis*), red sprangletop (*Leptochloa panicea*), annual bluegrass (*Poa annua* L.), black grass (*Alopecurus mvosuroides* Huds.), cholorado bluestem (*Aqropyron tsukushiense* (Honda) Ohwi), broadleaf signalgrass (*Brachiaria platyphylla* Nash), southern sandbur (*Cenchrus echinatus* L.), Italian ryegrass (*Lolium multiflorum* Lam.), and bermudagrass (*Cynodon dactylon* Pers.); cyperaceae such as rice flatsedge (*Cyperus iria* L.), purple nutsedge (*Cyperus rotundus* L.), yellow nutsedge (*Cyperus esculentus* L.), Japanese bulrush (*Scirpus luncoides*), flatsedge (*Cyperus serotinus*), small-flower umbrellaplant (*Cyperus difformis*), slender spikerush (*Eleocharis acicularis), and water chestnut *Eleocharis kuroguwai*); alismataceae such as Japanese ribbon waparo (*Sagittaria pygmaea*), arrow-head (*Sagittaria trifolia*), and narrowleaf waterplantain (*Alisma canaliculatum*); pontederiaceae such as monochoria (*Monochoria vaginalis*), and monochoria species (*Monochoria korsakowii*); scrophulariaceae such as false pimpernel (*Lindernia pyxidaria*), and abunome (*Dopatrium junceum*); lythraceae such as toothcup (*Rotala india*), and red stem (*Ammannia multiflora*); elatinaceae such as long stem waterwort (*Elatine triandra* SCHK.); malvaceae such as velvetleaf (*Abutilon theophrasti* MEDIC.), and prickly sida (*Sida spinosa* L.); compositae such as common cocklebur (*Xanthium strumarium* L.), common ragweed (*Ambrosia elatior* L.), thistle (*Breea setosa* (BIEB.) KITAM.), hairy galinsoga (*Galinsoqa ciliata* Blake), wild chamomile (*Matricaria chamomilla* L.); solanaceae such as black nightshade (*Solanum nigrum* L.), and jimsonweed (*Datura stramonium*); amaranthaceae such as slender amaranth (*Amaranthus viridis* L.), and redroot pigweed (*Amaranthus retroflexus* L.); polygonaceeae such as pale smartweed (*Polygonum lapathifolium* L.), ladysthumb (*Polygonum persicaria* L.), wild buckwheat (*Polygonum convolvulus* L.), and knotweed (*Polygonum aviculare* L.); cruciferae such as flexuous bittercress (*Cardamine flexuosa* WITH.), shepherd's-purse (*Capsella bursa-pastoris* Medik.), and indian mustard (*Brassica juncea* Czem.); convolvulaceae such as tall morningglory (*Ipomoea purpurea* L.), field bindweed (*Calvstegia arvensis* L.), and ivyleaf morningglory (*Ipomoea hederacea* Jacq.); Chenopodiaceae such as common lambsquarters (*Chenopodium album* L.), and mexican burningbush (*Kochia scoparia* Schrad.); Portulacaceae such as common purslane (*Portulaca oleracea* L.); leguminosae such as sicklepod (*Cassia obtusifolia* L.); caryophyllaceae such as common chickweed (*Stellaria media* L.); labiatae such as henbit (*Lamium amplexicaule* L.); rubiaceae such as catchweed (*Galium spurium* L.); euphorbiaceae such as threeseeded copperleaf (*Acalvpha australis* L.); and Commelinaceae such as common dayflower (*Commelina communis* L.).

Therefore, it can be effectively used for selectively controlling noxious weeds or nonselectively controlling noxious weeds in cultivation of useful crops such as corn (*Zea mays* L.), soybean (*Glycine max* Merr.), cotton (*Gossypium* spp.), wheat (*Triticum* spp.), rice (*Oryza sativa* L.), barley (*Hordeum vulgare* L.), rye (*Secale cereale* L.), oat (*Avena sativa* L.), sorgo (*Sorghum bicolor* Moench), rape (*Brassica napus* L.), sunflower (*Helianthus annuus* L.), sugar beet (*Beta vulgaris* L.), sugar cane (*Saccharum officinarum* L.), japanese lawngrass (*Zoysia japonica* stend), peanut (*Arachis hvpogaea* L.), flax (*Linum usitatissimum* L.), tobacco (*Nicotiana tabacum* L.), and coffee (*Coffea* spp.). Particularly, the herbicidal composition of the present invention is effectively used for selectively controlling noxious weeds in cultivation of corn, soybean, cotton, wheat, rice, rape, sunflower, sugar beet, sugar cane, japanese lawngrass, peanut, flax, tobacco, coffee, and the like, and among these, especially corn, wheat, rice, japanese lawngrass and the like. Its application range extends not only to crop plant fields but also to agricultural fields such as orchards and mulberry fields and non-agricultural fields such as forest land, farm roads, play grounds, factory sites and lawn fields.

Now, among the compounds of the formula (I), typical examples of the compound wherein T is $T^1$, Q is —C(O)$SR^3$, and Z is $Z^1$, are shown in Table a1; typical examples of the compound wherein T is $T^1$, Q is hydrogen, and Z is $Z^1$, are shown in Table a2; typical examples of the compound wherein T is $T^2$, and Z is $Z^1$, are shown in Table a3; typical examples of the compound wherein T is $T^1$, Q is -A-O—C(O)$OR^{10}$, and Z is $Z^1$, are shown in Table a4; and typical examples of the compound wherein T is $T^3$, and Z is $Z^2$, are shown in Table a5. However, the compounds of the formula (I) in the present invention are not limited thereto. These compounds can be prepared in accordance with various production methods disclosed in e.g. WO2007/069771, U.S. Pat. No. 6,376,429, WO2008/068907 and WO2001/094339. Further, the following compound No. 4-320 can be prepared in accordance with the following Reference Preparation Example.

Reference Preparation Example

Preparation of 1-(1-ethyl-4-(3-(2-methoxyethoxy)-2-methyl-4-(methylsulfonyl)benzoyl)-1H-pyrazol-5-yloxy)ethyl methyl carbonate (the Following Compound No. 4-320)

5-Hydroxy-1-ethylpyrazol-4-yl 3-(2-methoxyethoxy)-2-methyl-4-(methylsulfonyl)phenyl ketone (300 mg) was dissolved in 2-butanone (10 mL), and potassium carbonate (130 mg) and tetrabutylammonium bromide (15 mg) were added. After stirring at room temperature for 10 minutes, 1-chloroethyl methyl carbonate (purity: 85%, 270 mg) was added at room temperature, followed by heating and refluxing for 3 hours. After completion of the reaction, the reaction mixture was cooled to room temperature and poured into water and then extracted with ethyl acetate. The organic layer was washed with 1N hydrochloric acid and a saturated sodium chloride aqueous solution, followed by drying over anhydrous sodium sulfate. The solvent was distilled off under reduced pressure. The obtained residue was purified by column chromatography with n-hexane:ethyl acetate=1:1, to obtain the desired product (180 mg) as slightly yellow solid. The NMR spectrum data of this product are as follows. $^1$H=NMR δppm (measuring instrument: JEOL-GSX (400 MHz), solvent: CDCl$_3$) 1.40 (3H, t, J=7.2 Hz), 1.77 (3H, d, J=5.2 Hz), 2.35 (3H, s), 2.94 (3H, s), 3.46 (3H, s), 3.71 (3H, s), 3.80 (2H, t, J=4.4 Hz), 4.05 (2H, m), 4.24 (2H, t, J=4.4 Hz), 6.78 (1H, q, J=5.2 Hz), 7.26 (1H, d, J=7.6 Hz), 7.28 (1H, s), 7.88 (1H, d, J=7.6 Hz).

In Tables a1 to a5, No. represents a compound No. Further, in Tables a1 to a5, Me represents a methyl group, Et an ethyl group, n-Pr a n-propyl group, i-Pr an isopropyl group, c-Pr a cyclopropyl group, s-Bu a secondary butyl group, t-Bu a tertiary butyl group, and Bn a benzyl group. Further, the left hand side of -A- is bonded to the pyrazole side, and the right hand side of -A- is bonded to the carbonate side.

TABLE a1

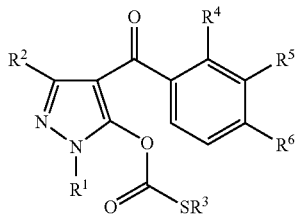

| No. | R¹ | R² | R³ | R⁴ | R⁵ | R⁶ |
|---|---|---|---|---|---|---|
| 1 | Me | H | Et | Me | $CO_2Me$ | $SO_2Me$ |
| 2 | Et | H | Et | Me | $CO_2Me$ | $SO_2Me$ |
| 3 | Me | H | Me | Me | $CO_2Me$ | $SO_2Me$ |
| 4 | Et | H | Me | Me | $CO_2Me$ | $SO_2Me$ |
| 5 | n-Pr | H | Et | Me | $CO_2Me$ | $SO_2Me$ |
| 6 | c-Pr | H | Et | Me | $CO_2Me$ | $SO_2Me$ |
| 7 | n-Pr | H | Me | Me | $CO_2Me$ | $SO_2Me$ |
| 8 | c-Pr | H | Me | Me | $CO_2Me$ | $SO_2Me$ |
| 9 | t-Bu | H | Et | Me | $CO_2Me$ | $SO_2Me$ |
| 10 | t-Bu | H | Me | Me | $CO_2Me$ | $SO_2Me$ |
| 11 | Me | Me | Et | Me | $CO_2Me$ | $SO_2Me$ |
| 12 | Et | H | Et | Me | $CO_2(i-Pr)$ | $SO_2Me$ |
| 13 | Me | H | Et | Me | $CO_2Et$ | $SO_2Me$ |
| 14 | Et | H | Et | Me | $CO_2Me$ | $NO_2$ |
| 15 | Et | H | Et | $SO_2Me$ | $CO_2Me$ | $CF_3$ |
| 16 | Et | H | Et | Me | $OCH_2CH_2OMe$ | $SO_2Me$ |
| 17 | Et | H | Et | Cl | $OCH_2CH_2OMe$ | $SO_2Me$ |
| 18 | Et | H | Et | Me | $CO_2Me$ | CN |
| 19 | Me | H | Et | Me | C(O)SMe | $SO_2Me$ |
| 20 | Et | H | Et | Me | C(O)SMe | $SO_2Me$ |
| 21 | Me | H | Me | Me | C(O)SEt | $SO_2Me$ |
| 22 | Et | H | Me | Me | C(O)SEt | $SO_2Me$ |
| 23 | Me | H | Et | Me | 2-(2-Oxolanyl)ethoxy | $SO_2Me$ |
| 24 | Me | H | Et | Me | 2-(2-(1,3-Dioxolanyl))ethoxy | $SO_2Me$ |
| 25 | Et | H | Et | Me | $CH_2OMe$ | $SO_2Me$ |
| 26 | Et | H | Et | Me | 2-Oxolanylmethoxymethyl | $SO_2Me$ |
| 27 | Me | H | Et | Cl | $CO_2Me$ | $SO_2Me$ |
| 28 | Et | H | Et | Cl | $CO_2Me$ | $SO_2Et$ |
| 29 | Me | H | Me | Cl | $CO_2Me$ | $SO_2Me$ |
| 30 | Et | H | Me | Br | $CO_2Me$ | $SO_2Me$ |
| 31 | Me | H | Et | Cl | C(O)SMe | $SO_2Me$ |
| 32 | Et | H | Et | Cl | C(O)SMe | $SO_2Me$ |
| 33 | Me | H | Et | Cl | C(O)SEt | $SO_2Me$ |
| 34 | Et | H | Et | Cl | C(O)SEt | $SO_2Me$ |
| 35 | Me | H | Et | Me | OMe | $SO_2Me$ |
| 36 | Me | H | Et | Me | OEt | $SO_2Me$ |
| 37 | Me | H | Et | Me | O(i-Pr) | $SO_2Me$ |
| 38 | Me | H | Et | Me | $OCHF_2$ | $SO_2Me$ |
| 39 | Me | H | Et | Me | O(n-Pr) | $SO_2Et$ |
| 40 | Me | H | Et | Cl | $CH_2OMe$ | $SO_2Me$ |
| 41 | Me | H | Et | Me | $OCO_2Me$ | $SO_2Me$ |
| 42 | Et | H | Et | Me | $OCO_2Me$ | $SO_2Me$ |
| 43 | Me | H | Me | Me | $OCO_2Me$ | $SO_2Me$ |
| 44 | Et | H | Me | Me | $OCO_2Me$ | $SO_2Me$ |
| 45 | Me | H | Et | Me | OC(O)SMe | $SO_2Me$ |
| 46 | Et | H | Et | Me | OC(O)SMe | $SO_2Me$ |
| 47 | Me | H | Me | Me | OC(O)SMe | $SO_2Me$ |
| 48 | Et | H | Me | Me | OC(O)SMe | $SO_2Me$ |
| 49 | Me | H | Et | Me | OC(O)SEt | $SO_2Me$ |
| 50 | Et | H | Et | Me | QC(O)SEt | $SO_2Me$ |
| 51 | Me | H | Me | Me | OC(O)SEt | $SO_2Me$ |
| 52 | Et | H | Me | Me | OC(O)SEt | $SO_2Me$ |
| 53 | Me | H | Et | Me | $OCH_2CH_2OMe$ | $SO_2Me$ |
| 54 | Me | H | Me | Me | $OCH_2CH_2OMe$ | $SO_2Et$ |
| 55 | Me | H | Et | Cl | $OCH_2CH_2OMe$ | $SO_2Me$ |
| 56 | Et | H | Et | Me | OEt | $SO_2Me$ |
| 57 | Et | H | Et | Cl | $CO_2Et$ | $SO_2Me$ |
| 58 | Et | H | Et | Cl | $CO_2(n-Pr)$ | $SO_2Me$ |
| 59 | Et | H | Et | Me | $CO_2Et$ | $SO_2Me$ |
| 60 | Et | H | Me | Me | $CO_2Et$ | $SO_2Me$ |
| 61 | Me | H | Et | Me | $CH_2OMe$ | $SO_2Me$ |
| 62 | Me | H | Et | Me | $CH_2CO_2Me$ | $SO_2Me$ |
| 63 | Me | H | Et | Me | $OCH_2CO_2Et$ | $SO_2Me$ |
| 64 | Me | H | Et | Me | O(n-Pr) | $SO_2Me$ |
| 65 | Et | H | Et | Me | O(n-Pr) | $SO_2Me$ |
| 66 | Et | H | Et | $SO_2Me$ | H | $CF_3$ |
| 67 | Me | H | Et | Me | $CH_2OCH_2CF_3$ | $SO_2Me$ |

TABLE a1-continued

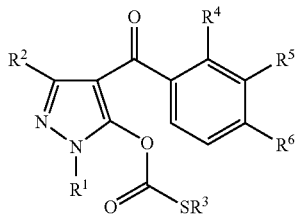

| No. | R¹ | R² | R³ | R⁴ | R⁵ | R⁶ |
|-----|----|----|----|----|----|----|
| 68 | Me | H | Et | Cl | CH$_2$OCH$_2$CF$_3$ | SO$_2$Me |
| 69 | Et | H | Et | Me | Cl | SO$_2$Me |
| 70 | Me | H | Et | Me | CH$_2$SO$_2$Me | SO$_2$Me |
| 71 | Me | H | Et | Me | CH$_2$OEt | SO$_2$Me |
| 72 | Me | H | Me | Cl | CH$_2$OMe | SO$_2$Me |
| 73 | Me | H | Et | Me | CH$_2$CH$_2$OMe | SO$_2$Me |
| 74 | Me | H | Et | Me | CH$_2$OCH$_2$CH$_2$OMe | SO$_2$Me |
| 75 | Me | H | Et | Me | OCH$_2$CH$_2$OEt | SO$_2$Me |
| 76 | Me | H | Et | Me | OCH$_2$CH$_2$Cl | SO$_2$Me |
| 77 | Me | H | Et | Me | OCH$_2$CF$_3$ | SO$_2$Me |
| 78 | Me | H | Et | Me | CH$_2$OCH$_2$OMe | SO$_2$Me |
| 79 | Me | H | Et | Me | OCH$_2$CH$_2$SMe | SO$_2$Me |
| 80 | Me | H | Et | Me | CN | SO$_2$Me |
| 81 | Me | H | Et | Me | CH$_2$CN | SO$_2$Me |
| 82 | Me | H | n-Pr | Me | CO$_2$Me | SO$_2$Me |
| 83 | Et | H | n-Pr | Me | CO$_2$Me | SO$_2$Me |
| 84 | Me | H | i-Pr | Me | CO$_2$Me | SO$_2$Me |
| 85 | Et | H | i-Pr | Me | CO$_2$Me | SO$_2$Me |
| 86 | Me | H | s-Bu | Me | CO$_2$Me | SO$_2$Me |
| 87 | Et | H | s-Bu | Me | CO$_2$Me | SO$_2$Me |
| 88 | Me | H | t-Bu | Me | CO$_2$Me | SO$_2$Me |
| 89 | Et | H | t-Bu | Me | CO$_2$Me | SO$_2$Me |
| 90 | Me | H | Bn | Me | CO$_2$Me | SO$_2$Me |
| 91 | Et | H | Bn | Me | CO$_2$Me | SO$_2$Me |
| 92 | Me | H | Et | Br | CO$_2$Me | SO$_2$Me |
| 93 | Et | H | Et | Cl | CO$_2$Me | SO$_2$Me |
| 94 | Me | H | Me | Br | CO$_2$Me | SO$_2$Me |
| 95 | Et | H | Me | Cl | CO$_2$Me | SO$_2$Me |
| 96 | Me | H | Allyl | Me | CO$_2$Me | SO$_2$Me |
| 97 | Et | H | Allyl | Me | CO$_2$Me | SO$_2$Me |
| 98 | Me | H | CH$_2$CH(CH$_3$)=CH$_2$ | Me | CO$_2$Me | SO$_2$Me |
| 99 | Et | H | CH$_2$CH(CH$_3$)=CH$_2$ | Me | CO$_2$Me | SO$_2$Me |
| 100 | Me | H | Et | Cl | OCH$_2$CH$_2$OCF$_3$ | SO$_2$Me |
| 101 | Et | H | Et | Cl | OCH$_2$CH$_2$OCF$_3$ | SO$_2$Me |
| 102 | Me | H | Et | Me | OCH$_2$CH$_2$OCF$_3$ | SO$_2$Me |
| 103 | Et | H | Et | Me | OCH$_2$CH$_2$OCF$_3$ | SO$_2$Me |
| 104 | Me | H | Et | CF$_3$ | OCH$_2$CH$_2$OCF$_3$ | SO$_2$Me |
| 105 | Et | H | Et | CF$_3$ | OCH$_2$CH$_2$OCF$_3$ | SO$_2$Me |
| 106 | Me | H | Et | Br | OCH$_2$CH$_2$OCF$_3$ | SO$_2$Me |
| 107 | Et | H | Et | Br | OCH$_2$CH$_2$OCF$_3$ | SO$_2$Me |
| 108 | Me | H | Et | SO$_2$Me | OCH$_2$CH$_2$OCF$_3$ | CF$_3$ |
| 109 | Et | H | Et | SO$_2$Me | OCH$_2$CH$_2$OCF$_3$ | CF$_3$ |
| 110 | Me | H | Et | Cl | OCH$_2$CH$_2$OCHClF | SO$_2$Me |
| 111 | Et | H | Et | Cl | OCH$_2$CH$_2$OCHClF | SO$_2$Me |
| 112 | Me | H | Et | Me | OCH$_2$CH$_2$OCHClF | SO$_2$Me |
| 113 | Et | H | Et | Me | OCH$_2$CH$_2$OCHClF | SO$_2$Me |
| 114 | Me | H | Et | CF$_3$ | OCH$_2$CH$_2$OCHClF | SO$_2$Me |
| 115 | Et | H | Et | CF$_3$ | OCH$_2$CH$_2$OCHClF | SO$_2$Me |
| 116 | Me | H | Et | Br | OCH$_2$CH$_2$OCHClF | SO$_2$Me |
| 117 | Et | H | Et | Br | OCH$_2$CH$_2$OCHClF | SO$_2$Me |
| 118 | Me | H | Et | SO$_2$Me | OCH$_2$CH$_2$OCHClF | CF$_3$ |
| 119 | Et | H | Et | SO$_2$Me | OCH$_2$CH$_2$OCHClF | CF$_3$ |
| 120 | Me | H | Et | Cl | OCH$_2$CHFOCF$_3$ | SO$_2$Me |
| 121 | Et | H | Et | Cl | OCH$_2$CHFOCF$_3$ | SO$_2$Me |
| 122 | Me | H | Et | Me | OCH$_2$CHFOCF$_3$ | SO$_2$Me |
| 123 | Me | H | Et | Cl | OCH$_2$CHFOMe | SO$_2$Me |
| 124 | Et | H | Et | Cl | OCH$_2$CHFOMe | SO$_2$Me |
| 125 | Me | H | Et | Me | OCH$_2$CHFOMe | SO$_2$Me |
| 126 | Et | H | Et | Me | OCH$_2$CHFOMe | SO$_2$Me |
| 127 | Me | H | Et | CF$_3$ | OCH$_2$CHFOMe | SO$_2$Me |
| 128 | Et | H | Et | CF$_3$ | OCH$_2$CHFOMe | SO$_2$Me |
| 129 | Me | H | Et | Br | OCH$_2$CHFOMe | SO$_2$Me |
| 130 | Et | H | Et | Br | OCH$_2$CHFOMe | SO$_2$Me |
| 131 | Me | H | Et | SO$_2$Me | OCH$_2$CHFOMe | CF$_3$ |
| 132 | Et | H | Et | SO$_2$Me | OCH$_2$CHFOMe | CF$_3$ |
| 133 | Me | H | Et | Cl | OCHFCH$_2$OCF$_3$ | SO$_2$Me |
| 134 | Et | H | Et | Cl | OCHFCH$_2$OCF$_3$ | SO$_2$Me |

TABLE a1-continued

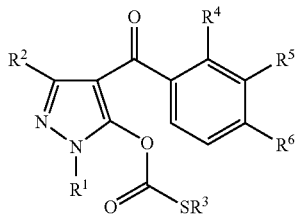

| No. | R¹ | R² | R³ | R⁴ | R⁵ | R⁶ |
|---|---|---|---|---|---|---|
| 135 | Me | H | Et | Cl | OCH$_2$CH$_2$OCF$_2$Cl | SO$_2$Me |
| 136 | Et | H | Et | Cl | OCH$_2$CH$_2$OCF$_2$Cl | SO$_2$Me |
| 137 | Me | H | Et | Me | OCH$_2$CH$_2$OCF$_2$Cl | SO$_2$Me |
| 138 | Et | H | Et | Me | OCH$_2$CH$_2$OCF$_2$Cl | SO$_2$Me |
| 139 | Me | H | Et | CF$_3$ | OCH$_2$CH$_2$OCF$_2$Cl | SO$_2$Me |
| 140 | Et | H | Et | CF$_3$ | OCH$_2$CH$_2$OCF$_2$Cl | SO$_2$Me |
| 141 | Me | H | Et | Br | OCH$_2$CH$_2$OCF$_2$Cl | SO$_2$Me |
| 142 | Et | H | Et | Br | OCH$_2$CH$_2$OCF$_2$Cl | SO$_2$Me |
| 143 | Me | H | Et | SO$_2$Me | OCH$_2$CH$_2$OCF$_2$Cl | CF$_3$ |
| 144 | Et | H | Et | SO$_2$Me | OCH$_2$CH$_2$OCF$_2$Cl | CF$_3$ |
| 145 | Me | H | Et | Cl | SCH$_2$CH$_2$OCH$_3$ | SO$_2$Me |
| 146 | Et | H | Et | Cl | SCH$_2$CH$_2$OCH$_3$ | SO$_2$Me |
| 147 | Me | H | Et | Me | SCH$_2$CH$_2$OCH$_3$ | SO$_2$Me |
| 148 | Et | H | Et | Me | SCH$_2$CH$_2$OCH$_3$ | SO$_2$Me |
| 149 | Me | H | Et | CF$_3$ | SCH$_2$CH$_2$OCH$_3$ | SO$_2$Me |
| 150 | Et | H | Et | CF$_3$ | SCH$_2$CH$_2$OCH$_3$ | SO$_2$Me |
| 151 | Me | H | Et | Br | SCH$_2$CH$_2$OCH$_3$ | SO$_2$Me |
| 152 | Et | H | Et | Br | SCH$_2$CH$_2$OCH$_3$ | SO$_2$Me |
| 153 | Me | H | Et | SO$_2$Me | SCH$_2$CH$_2$OCH$_3$ | CF$_3$ |
| 154 | Et | H | Et | SO$_2$Me | SCH$_2$CH$_2$OCH$_3$ | CF$_3$ |
| 155 | Me | H | Et | Cl | SCH$_2$CH$_2$OCF$_3$ | SO$_2$Me |
| 156 | Et | H | Et | Cl | SCH$_2$CH$_2$OCF$_3$ | SO$_2$Me |
| 157 | Me | H | Et | Me | SCH$_2$CH$_2$OCF$_3$ | SO$_2$Me |
| 158 | Et | H | Et | Me | SCH$_2$CH$_2$OCF$_3$ | SO$_2$Me |
| 159 | Me | H | Et | CF$_3$ | SCH$_2$CH$_2$OCF$_3$ | SO$_2$Me |
| 160 | Et | H | Et | CF$_3$ | SCH$_2$CH$_2$OCF$_3$ | SO$_2$Me |
| 161 | Me | H | Et | Br | SCH$_2$CH$_2$OCF$_3$ | SO$_2$Me |
| 162 | Et | H | Et | Br | SCH$_2$CH$_2$OCF$_3$ | SO$_2$Me |
| 163 | Me | H | Et | SO$_2$Me | SCH$_2$CH$_2$OCF$_3$ | CF$_3$ |
| 164 | Et | H | Et | SO$_2$Me | SCH$_2$CH$_2$OCF$_3$ | CF$_3$ |
| 165 | Me | H | Et | Cl | SCH$_2$CH$_2$SCH$_3$ | SO$_2$Me |
| 166 | Et | H | Et | Cl | SCH$_2$CH$_2$SCH$_3$ | SO$_2$Me |
| 167 | Me | H | Et | Me | SCH$_2$CH$_2$SCH$_3$ | SO$_2$Me |
| 168 | Et | H | Et | Me | SCH$_2$CH$_2$SCH$_3$ | SO$_2$Me |
| 169 | Me | H | Et | CF$_3$ | SCH$_2$CH$_2$SCH$_3$ | SO$_2$Me |
| 170 | Et | H | Et | CF$_3$ | SCH$_2$CH$_2$SCH$_3$ | SO$_2$Me |
| 171 | Me | H | Et | Br | SCH$_2$CH$_2$SCH$_3$ | SO$_2$Me |
| 172 | Et | H | Et | Br | SCH$_2$CH$_2$SCH$_3$ | SO$_2$Me |
| 173 | Me | H | Et | SO$_2$Me | SCH$_2$CH$_2$SCH$_3$ | CF$_3$ |
| 174 | Et | H | Et | SO$_2$Me | SCH$_2$CH$_2$SCH$_3$ | CF$_3$ |
| 175 | Me | H | Et | Cl | SCH$_2$CH$_2$SCF$_3$ | SO$_2$Me |
| 176 | Et | H | Et | Cl | SCH$_2$CH$_2$SCF$_3$ | SO$_2$Me |
| 177 | Me | H | Et | Me | SCH$_2$CH$_2$SCF$_3$ | SO$_2$Me |
| 178 | Et | H | Et | Me | SCH$_2$CH$_2$SCF$_3$ | SO$_2$Me |
| 179 | Me | H | Et | CF$_3$ | SCH$_2$CH$_2$SCF$_3$ | SO$_2$Me |
| 180 | Et | H | Et | CF$_3$ | SCH$_2$CH$_2$SCF$_3$ | SO$_2$Me |
| 181 | Me | H | Et | Br | SCH$_2$CH$_2$SCF$_3$ | SO$_2$Me |
| 182 | Et | H | Et | Br | SCH$_2$CH$_2$SCF$_3$ | SO$_2$Me |
| 183 | Me | H | Et | SO$_2$Me | SCH$_2$CH$_2$SCF$_3$ | CF$_3$ |
| 184 | Et | H | Et | SO$_2$Me | SCH$_2$CH$_2$SCF$_3$ | CF$_3$ |
| 185 | Me | H | Et | Cl | OCH$_2$CH(CH$_3$)OCH$_3$ | SO$_2$Me |
| 186 | Et | H | Et | Cl | OCH$_2$CH(CH$_3$)OCH$_3$ | SO$_2$Me |
| 187 | Me | H | Et | Me | OCH$_2$CH(CH$_3$)OCH$_3$ | SO$_2$Me |
| 188 | Et | H | Et | Me | OCH$_2$CH(CH$_3$)OCH$_3$ | SO$_2$Me |
| 189 | Me | H | Et | CF$_3$ | OCH$_2$CH(CH$_3$)OCH$_3$ | SO$_2$Me |
| 190 | Et | H | Et | CF$_3$ | OCH$_2$CH(CH$_3$)OCH$_3$ | SO$_2$Me |
| 191 | Me | H | Et | Br | OCH$_2$CH(CH$_3$)OCH$_3$ | SO$_2$Me |
| 192 | Et | H | Et | Br | OCH$_2$CH(CH$_3$)OCH$_3$ | SO$_2$Me |
| 193 | Me | H | Et | SO$_2$Me | OCH$_2$CH(CH$_3$)OCH$_3$ | CF$_3$ |
| 194 | Et | H | Et | SO$_2$Me | OCH$_2$CH(CH$_3$)OCH$_3$ | CF$_3$ |
| 195 | Me | H | Et | Cl | OCH$_2$CF$_2$OCH$_3$ | SO$_2$Me |
| 196 | Et | H | Et | Cl | OCH$_2$CF$_2$OCH$_3$ | SO$_2$Me |
| 197 | Me | H | Et | Me | OCH$_2$CF$_2$OCH$_3$ | SO$_2$Me |
| 198 | Et | H | Et | Me | OCH$_2$CF$_2$OCH$_3$ | SO$_2$Me |
| 199 | Me | H | Et | CF$_3$ | OCH$_2$CF$_2$OCH$_3$ | SO$_2$Me |
| 200 | Et | H | Et | CF$_3$ | OCH$_2$CF$_2$OCH$_3$ | SO$_2$Me |
| 201 | Me | H | Et | Br | OCH$_2$CF$_2$OCH$_3$ | SO$_2$Me |

TABLE a1-continued

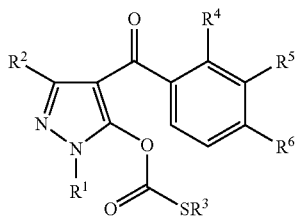

| No. | R¹ | R² | R³ | R⁴ | R⁵ | R⁶ |
|---|---|---|---|---|---|---|
| 202 | Et | H | Et | Br | OCH₂CF₂OCH₃ | SO₂Me |
| 203 | Me | H | Et | SO₂Me | OCH₂CF₂OCH₃ | CF₃ |
| 204 | Et | H | Et | SO₂Me | OCH₂CF₂OCH₃ | CF₃ |
| 205 | Me | H | i-Pr | Me | OCH₂CH₂OCH₃ | SO₂Me |
| 206 | Et | H | i-Pr | Me | OCH₂CH₂OCH₃ | SO₂Me |
| 207 | Me | H | Et | Me | OCH₂CH(OCH₃)₂ | SO₂Me |
| 208 | Me | H | Et | Me | CH₂N(Me)CH₂CN | SO₂Me |
| 209 | Me | H | Et | Me | (Tetrahydrofuran-2-yl)methoxy | SO₂Me |
| 210 | Me | H | Et | Cl | SMe | SO₂Me |
| 211 | Me | H | Et | Cl | Cl | SO₂Me |
| 212 | Me | H | Et | Cl | OMe | SO₂Me |
| 213 | Me | H | Et | Me | (Tetrahydro-2H-pyran-2-yl)methoxy | SO₂Me |
| 214 | Me | H | Et | Me | Tetrahydrofuran-3-yloxy | SO₂Me |
| 215 | Me | H | Et | Me | OCH₂CH₂CH₂OMe | SO₂Me |
| 216 | Me | H | n-Pr | Me | OCH₂CH₂OMe | SO₂Me |
| 217 | Et | H | s-Bu | Cl | C(O)OMe | SO₂Me |
| 218 | Et | H | Et | Cl | 2-(1,3-Dioxolan-2-yl)ethoxy | SO₂Me |
| 219 | Me | H | Et | Me | Propargyloxy | SO₂Me |
| 220 | Me | H | Et | Me | (Tetrahydrofuran-3-yloxy)methyl | SO₂Me |
| 221 | Me | H | Et | Cl | SO₂Me | SO₂Me |
| 222 | Me | H | Et | Me | (CH₂)₆Me | SO₂Me |
| 223 | Me | H | Et | Me | CH₂CH₂CH₂OMe | SO₂Me |
| 224 | Et | H | Et | Cl | (1,3-Dioxolan-2-yl)methoxy | SO₂Me |
| 225 | Me | H | Et | Me | CH₂N[C(O)SEt]CH₂CN | SO₂Me |
| 226 | Me | H | Et | Me | CH=CHCN | SO₂Me |
| 227 | Me | H | Et | Me | CH₂CH₂CN | SO₂Me |
| 228 | Me | H | Et | Me | CH₂SCN | SO₂Me |
| 229 | Me | H | Et | Me | CH₂C(S)NH₂ | SO₂Me |
| 230 | Me | H | Me | Me | OCH₂CH₂OMe | SO₂Me |
| 231 | Et | H | Me | Me | OCH₂CH₂OMe | SO₂Me |
| 232 | Et | H | n-Pr | Me | OCH₂CH₂OMe | SO₂Me |
| 233 | Me | H | Et | Me | OCH(CH₃)CH₂OMe | SO₂Me |
| 234 | Et | H | Et | Me | OCH₂CH(Et)OMe | SO₂Me |
| 235 | Me | H | Et | Me | (1,3-Dioxolan-2-yl)methyl | SO₂Me |
| 236 | Me | H | s-Bu | Me | OCH₂CH₂OMe | SO₂Me |
| 237 | Me | H | Et | Me | CH₂O(i-Pr) | SO₂Me |
| 238 | Me | H | t-Bu | Me | OCH₂CH₂OMe | SO₂Me |
| 239 | Me | H | CH₂CO₂Me | Me | OCH₂CH₂OMe | SO₂Me |
| 240 | Et | H | c-Pr | Me | CO₂Me | SO₂Me |
| 241 | Et | H | c-Pr | Me | CO₂(i-Pr) | SO₂Me |

TABLE a2

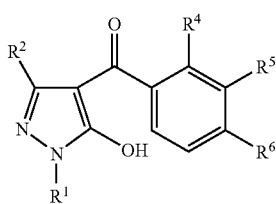

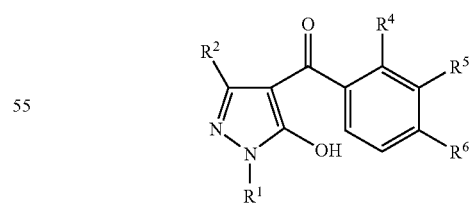

| No. | R¹ | R² | R⁴ | R⁵ | R⁶ |
|---|---|---|---|---|---|
| 2-1 | Me | H | Me | CO₂Me | SO₂Me |
| 2-2 | Et | H | Me | CO₂Me | SO₂Me |
| 2-3 | Et | H | Me | CO₂(i-Pr) | SO₂Me |
| 2-4 | Me | H | Cl | CO₂Et | SO₂Me |
| 2-5 | Et | H | Me | CO₂Me | CF₃ |
| 2-6 | Et | H | Me | OCH₂CH₂OMe | SO₂Me |
| 2-7 | Et | H | SO₂Me | CO₂Me | SO₂Me |
| 2-8 | Me | H | Me | C(O)SMe | SO₂Me |
| 2-9 | Me | H | Me | C(O)SEt | SO₂Me |
| 2-10 | Me | H | Me | 2-(2-Oxolanyl)ethoxy | SO₂Me |
| 2-11 | Me | H | Me | 2-(2-(1,3-Dioxolanyl)ethoxy | SO₂Me |
| 2-12 | Et | H | Me | CH₂OMe | SO₂Me |

TABLE a2-continued

| No. | R¹ | R² | R⁴ | R⁵ | R⁶ |
|---|---|---|---|---|---|
| 2-13 | Et | H | Me | 2-Oxolanylmethoxymethyl | SO₂Me |
| 2-14 | Me | H | Cl | CO₂Me | SO₂Me |
| 2-15 | Et | H | Cl | CO₂Me | SO₂Et |
| 2-16 | Me | H | Cl | C(O)SMe | SO₂Me |
| 2-17 | Me | H | Cl | C(O)SEt | SO₂Me |
| 2-18 | Me | H | Me | OMe | SO₂Me |
| 2-19 | Me | H | Me | OEt | SO₂Me |
| 2-20 | Me | H | Me | O(i-Pr) | SO₂Me |
| 2-21 | Me | H | Me | OCHF₂ | SO₂Me |
| 2-22 | Me | H | Me | O(n-Pr) | SO₂Et |
| 2-23 | Me | H | Cl | CH₂OMe | SO₂Me |
| 2-24 | Me | H | Me | OCO₂Me | SO₂Me |
| 2-25 | Me | H | Me | OC(O)SMe | SO₂Me |
| 2-26 | Me | H | Me | OC(O)SEt | SO₂Me |
| 2-27 | Me | H | Me | OCH₂CH₂OMe | SO₂Me |
| 2-28 | Et | H | Me | OEt | SO₂Me |
| 2-29 | Et | H | Cl | CO₂Et | SO₂Me |
| 2-30 | Et | H | Cl | CO₂(n-Pr) | SO₂Me |
| 2-31 | Et | H | Me | CO₂Et | SO₂Me |
| 2-32 | Me | H | Me | CH₂CO₂Me | SO₂Me |
| 2-33 | Me | H | Me | OCH₂CO₂Et | SO₂Me |
| 2-34 | Me | H | Me | O(n-Pr) | SO₂Me |
| 2-35 | Me | H | Me | CH₂OCH₂CF₃ | SO₂Me |
| 2-36 | Me | H | Cl | CH₂OCH₂CF₃ | SO₂Me |
| 2-37 | Et | H | Me | Cl | SO₂Me |
| 2-38 | Me | H | Me | CH₂SO₂Me | SO₂Me |
| 2-39 | Me | H | Me | CH₂OEt | SO₂Me |
| 2-40 | Me | H | Cl | CH₂OMe | SO₂Me |
| 2-41 | Me | H | Me | CH₂CH₂OMe | SO₂Me |
| 2-42 | Me | H | Me | CH₂OCH₂CH₂OMe | SO₂Me |
| 2-43 | Me | H | Me | OCH₂CH₂OEt | SO₂Me |
| 2-44 | Me | H | Me | OCH₂CH₂Cl | SO₂Me |
| 2-45 | Me | H | Me | OCH₂CF₃ | SO₂Me |
| 2-46 | Me | H | Me | CH₂OCH₂OMe | SO₂Me |
| 2-47 | Me | H | Me | OCH₂CH₂SMe | SO₂Me |
| 2-48 | Me | H | Me | CN | SO₂Me |
| 2-49 | Me | H | Me | CH₂CN | SO₂Me |
| 2-50 | Me | H | Br | CO₂Me | SO₂Me |
| 2-51 | Et | H | Cl | CO₂Me | SO₂Me |
| 2-52 | Me | H | Cl | OCH₂CH₂OCF₃ | SO₂Me |
| 2-53 | Et | H | Cl | OCH₂CH₂OCF₃ | SO₂Me |
| 2-54 | Me | H | Me | OCH₂CH₂OCF₃ | SO₂Me |
| 2-55 | Et | H | Me | OCH₂CH₂OCF₃ | SO₂Me |
| 2-56 | Me | H | CF₃ | OCH₂CH₂OCF₃ | SO₂Me |
| 2-57 | Et | H | CF₃ | OCH₂CH₂OCF₃ | SO₂Me |
| 2-58 | Me | H | Br | OCH₂CH₂OCF₃ | SO₂Me |
| 2-59 | Et | H | Br | OCH₂CH₂OCF₃ | SO₂Me |
| 2-60 | Me | H | SO₂Me | OCH₂CH₂OCF₃ | CF₃ |
| 2-61 | Et | H | SO₂Me | OCH₂CH₂OCF₃ | CF₃ |
| 2-62 | Me | H | Cl | OCH₂CH₂OCHClF | SO₂Me |
| 2-63 | Et | H | Cl | OCH₂CH₂OCHClF | SO₂Me |
| 2-64 | Me | H | Me | OCH₂CH₂OCHClF | SO₂Me |
| 2-65 | Et | H | Me | OCH₂CH₂OCHClF | SO₂Me |
| 2-66 | Me | H | CF₃ | OCH₂CH₂OCHClF | SO₂Me |
| 2-67 | Et | H | CF₃ | OCH₂CH₂OCHClF | SO₂Me |
| 2-68 | Me | H | Br | OCH₂CH₂OCHClF | SO₂Me |
| 2-69 | Et | H | Br | OCH₂CH₂OCHClF | SO₂Me |
| 2-70 | Me | H | SO₂Me | OCH₂CH₂OCHClF | CF₃ |
| 2-71 | Et | H | SO₂Me | OCH₂CH₂OCHClF | CF₃ |
| 2-72 | Me | H | Cl | OCH₂CHFOCF₃ | SO₂Me |
| 2-73 | Et | H | Cl | OCH₂CHFOCF₃ | SO₂Me |
| 2-74 | Me | H | Me | OCH₂CHFOCF₃ | SO₂Me |
| 2-75 | Me | H | Cl | OCH₂CHFOMe | SO₂Me |
| 2-76 | Et | H | Cl | OCH₂CHFOMe | SO₂Me |
| 2-77 | Me | H | Me | OCH₂CHFOMe | SO₂Me |
| 2-78 | Et | H | Me | OCH₂CHFOMe | SO₂Me |
| 2-79 | Me | H | CF₃ | OCH₂CHFOMe | SO₂Me |
| 2-80 | Et | H | CF₃ | OCH₂CHFOMe | SO₂Me |
| 2-81 | Me | H | Br | OCH₂CHFOMe | SO₂Me |
| 2-82 | Et | H | Br | OCH₂CHFOMe | SO₂Me |
| 2-83 | Me | H | SO₂Me | OCH₂CHFOMe | CF₃ |
| 2-84 | Et | H | SO₂Me | OCH₂CHFOMe | CF₃ |
| 2-85 | Me | H | Cl | OCHFCH₂OCF₃ | SO₂Me |
| 2-86 | Et | H | Cl | OCHFCH₂OCF₃ | SO₂Me |
| 2-87 | Me | H | Cl | OCH₂CH₂OCF₂Cl | SO₂Me |
| 2-88 | Et | H | Cl | OCH₂CH₂OCF₂Cl | SO₂Me |
| 2-89 | Me | H | Me | OCH₂CH₂OCF₂Cl | SO₂Me |
| 2-90 | Et | H | Me | OCH₂CH₂OCF₂Cl | SO₂Me |
| 2-91 | Me | H | CF₃ | OCH₂CH₂OCF₂Cl | SO₂Me |
| 2-92 | Et | H | CF₃ | OCH₂CH₂OCF₂Cl | SO₂Me |
| 2-93 | Me | H | Br | OCH₂CH₂OCF₂Cl | SO₂Me |
| 2-94 | Et | H | Br | OCH₂CH₂OCF₂Cl | SO₂Me |
| 2-95 | Me | H | SO₂Me | OCH₂CH₂OCF₂Cl | CF₃ |
| 2-96 | Et | H | SO₂Me | OCH₂CH₂OCF₂Cl | CF₃ |
| 2-97 | Me | H | Cl | SCH₂CH₂OCH₃ | SO₂Me |
| 2-98 | Et | H | Cl | SCH₂CH₂OCH₃ | SO₂Me |
| 2-99 | Me | H | Me | SCH₂CH₂OCH₃ | SO₂Me |
| 2-100 | Et | H | Me | SCH₂CH₂OCH₃ | SO₂Me |
| 2-101 | Me | H | CF₃ | SCH₂CH₂OCH₃ | SO₂Me |
| 2-102 | Et | H | CF₃ | SCH₂CH₂OCH₃ | SO₂Me |
| 2-103 | Me | H | Br | SCH₂CH₂OCH₃ | SO₂Me |
| 2-104 | Et | H | Br | SCH₂CH₂OCH₃ | SO₂Me |
| 2-105 | Me | H | SO₂Me | SCH₂CH₂OCH₃ | CF₃ |
| 2-106 | Et | H | SO₂Me | SCH₂CH₂OCH₃ | CF₃ |
| 2-107 | Me | H | Cl | SCH₂CH₂OCF₃ | SO₂Me |
| 2-108 | Et | H | Cl | SCH₂CH₂OCF₃ | SO₂Me |
| 2-109 | Me | H | Me | SCH₂CH₂OCF₃ | SO₂Me |
| 2-110 | Et | H | Me | SCH₂CH₂OCF₃ | SO₂Me |
| 2-111 | Me | H | CF₃ | SCH₂CH₂OCF₃ | SO₂Me |
| 2-112 | Et | H | CF₃ | SCH₂CH₂OCF₃ | SO₂Me |
| 2-113 | Me | H | Br | SCH₂CH₂OCF₃ | SO₂Me |
| 2-114 | Et | H | Br | SCH₂CH₂OCF₃ | SO₂Me |
| 2-115 | Me | H | SO₂Me | SCH₂CH₂OCF₃ | CF₃ |
| 2-116 | Et | H | SO₂Me | SCH₂CH₂OCF₃ | CF₃ |
| 2-117 | Me | H | Cl | SCH₂CH₂SCH₃ | SO₂Me |
| 2-118 | Et | H | Cl | SCH₂CH₂SCH₃ | SO₂Me |
| 2-119 | Me | H | Me | SCH₂CH₂SCH₃ | SO₂Me |
| 2-120 | Et | H | Me | SCH₂CH₂SCH₃ | SO₂Me |
| 2-121 | Me | H | CF₃ | SCH₂CH₂SCH₃ | SO₂Me |
| 2-122 | Et | H | CF₃ | SCH₂CH₂SCH₃ | SO₂Me |
| 2-123 | Me | H | Br | SCH₂CH₂SCH₃ | SO₂Me |
| 2-124 | Et | H | Br | SCH₂CH₂SCH₃ | SO₂Me |
| 2-125 | Me | H | SO₂Me | SCH₂CH₂SCH₃ | CF₃ |
| 2-126 | Et | H | SO₂Me | SCH₂CH₂SCH₃ | CF₃ |
| 2-127 | Me | H | Cl | SCH₂CH₂SCF₃ | SO₂Me |
| 2-128 | Et | H | Cl | SCH₂CH₂SCF₃ | SO₂Me |
| 2-129 | Me | H | Me | SCH₂CH₂SCF₃ | SO₂Me |
| 2-130 | Et | H | Me | SCH₂CH₂SCF₃ | SO₂Me |
| 2-131 | Me | H | CF₃ | SCH₂CH₂SCF₃ | SO₂Me |
| 2-132 | Et | H | CF₃ | SCH₂CH₂SCF₃ | SO₂Me |
| 2-133 | Me | H | Br | SCH₂CH₂SCF₃ | SO₂Me |
| 2-134 | Et | H | Br | SCH₂CH₂SCF₃ | SO₂Me |
| 2-135 | Me | H | SO₂Me | SCH₂CH₂SCF₃ | CF₃ |
| 2-136 | Et | H | SO₂Me | SCH₂CH₂SCF₃ | CF₃ |
| 2-137 | Me | H | Cl | OCH₂CH(CH₃)OCH₃ | SO₂Me |
| 2-138 | Et | H | Cl | OCH₂CH(CH₃)OCH₃ | SO₂Me |
| 2-139 | Me | H | Me | OCH₂CH(CH₃)OCH₃ | SO₂Me |
| 2-140 | Et | H | Me | OCH₂CH(CH₃)OCH₃ | SO₂Me |
| 2-141 | Me | H | CF₃ | OCH₂CH(CH₃)OCH₃ | SO₂Me |
| 2-142 | Et | H | CF₃ | OCH₂CH(CH₃)OCH₃ | SO₂Me |
| 2-143 | Me | H | Br | OCH₂CH(CH₃)OCH₃ | SO₂Me |
| 2-144 | Et | H | Br | OCH₂CH(CH₃)OCH₃ | SO₂Me |

TABLE a2-continued

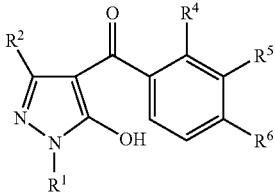

| No. | R¹ | R² | R⁴ | R⁵ | R⁶ |
|---|---|---|---|---|---|
| 2-145 | Me | H | SO₂Me | OCH₂CH(CH₃)OCH₃ | CF₃ |
| 2-146 | Et | H | SO₂Me | OCH₂CH(CH₃)OCH₃ | CF₃ |
| 2-147 | Me | H | Cl | OCH₂CF₂OCH₃ | SO₂Me |
| 2-148 | Et | H | Cl | OCH₂CF₂OCH₃ | SO₂Me |
| 2-149 | Me | H | Me | OCH₂CF₂OCH₃ | SO₂Me |
| 2-150 | Et | H | Me | OCH₂CF₂OCH₃ | SO₂Me |
| 2-151 | Me | H | CF₃ | OCH₂CF₂OCH₃ | SO₂Me |
| 2-152 | Et | H | CF₃ | OCH₂CF₂OCH₃ | SO₂Me |
| 2-153 | Me | H | Br | OCH₂CF₂OCH₃ | SO₂Me |
| 2-154 | Et | H | Br | OCH₂CF₂OCH₃ | SO₂Me |
| 2-155 | Me | H | SO₂Me | OCH₂CF₂OCH₃ | CF₃ |
| 2-156 | Et | H | SO₂Me | OCH₂CF₂OCH₃ | CF₃ |
| 2-157 | Me | H | Me | OCH₂CH₂OCH₃ | SO₂Me |
| 2-158 | Et | H | Me | OCH₂CH₂OCH₃ | SO₂Me |
| 2-159 | Me | H | Me | OCH₂CH(OCH₃)₂ | SO₂Me |
| 2-160 | Me | H | Me | CH₂N(Me)CH₂CN | SO₂Me |
| 2-161 | Me | H | Me | (Tetrahydrofuran-2-yl)methoxy | SO₂Me |
| 2-162 | Me | H | Cl | SMe | SO₂Me |
| 2-163 | Me | H | Cl | Cl | SO₂Me |
| 2-164 | Me | H | Cl | OMe | SO₂Me |
| 2-165 | Me | H | Me | (Tetrahydro-2H-pyran-2-yl)methoxy | SO₂Me |
| 2-166 | Me | H | Cl | OCH₂CH₂OMe | SO₂Me |
| 2-167 | Me | H | Me | Tetrahydrofuran-3-yloxy | SO₂Me |
| 2-168 | Me | H | Me | OCH₂CH₂OMe | SO₂Me |
| 2-169 | Et | H | Cl | (1,3-Dioxolan-2-yl)ethoxy | SO₂Me |
| 2-170 | Me | H | Me | Propargyloxy | SO₂Me |
| 2-171 | Me | H | Me | (Tetrahydro-3-yloxy)methyl | SO₂Me |
| 2-172 | Me | H | Cl | SO₂Me | SO₂Me |
| 2-173 | Me | H | Me | (CH₂)₆Me | SO₂Me |
| 2-174 | Me | H | Me | CH₂CH₂CH₂OMe | SO₂Me |
| 2-175 | Et | H | Cl | (1,3-Dioxolan-2-yl)methoxy | SO₂Me |
| 2-176 | Me | H | Me | CH₂N[C(O)SEt]CH₂CN | SO₂Me |
| 2-177 | Me | H | Me | CH=CHCN | SO₂Me |
| 2-178 | Me | H | Me | CH₂CH₂CN | SO₂Me |
| 2-179 | Me | H | Me | CH₂SCN | SO₂Me |
| 2-180 | Me | H | Me | CH₂C(S)NH₂ | SO₂Me |
| 2-181 | Me | H | Me | OCH(CH₃)CH₂OMe | SO₂Me |
| 2-182 | Me | H | Me | OCH₂CH(Et)OMe | SO₂Me |
| 2-183 | Me | H | Me | (1,3-Dioxolan-2-yl)methyl | SO₂Me |
| 2-184 | Me | H | Me | CH₂O(i-Pr) | SO₂Me |
| 2-185 | Me | H | Me | CH₂OMe | SO₂Me |
| 2-186 | Me | H | Me | OCH₂CH₂CH₂CH₃ | SO₂Me |
| 2-187 | Me | H | Me | OCH₂CH(Me)₂ | SO₂Me |

TABLE a3

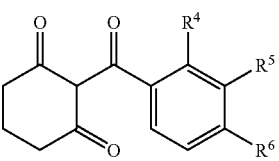

| No. | R⁴ | R⁵ | R⁶ |
|---|---|---|---|
| 3-1 | Me | CO₂Me | SO₂Me |
| 3-2 | Me | CO₂(i-Pr) | SO₂Me |
| 3-3 | Cl | CO₂Et | SO₂Me |

TABLE a3-continued

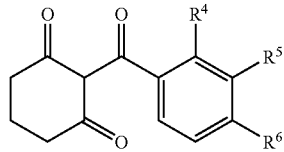

| No. | R⁴ | R⁵ | R⁶ |
|---|---|---|---|
| 3-4 | Me | CO₂Me | CF₃ |
| 3-5 | Me | OCH₂CH₂OMe | SO₂Me |
| 3-6 | SO₂Me | CO₂Me | CN |
| 3-7 | Me | C(O)SMe | SO₂Me |
| 3-8 | Me | C(O)SEt | SO₂Me |
| 3-9 | Me | 2-(2-Oxolanyl)ethoxy | SO₂Me |
| 3-10 | Me | 2-(2-(1,3-Dioxolanyl)ethoxy | SO₂Me |
| 3-11 | Me | CH₂OMe | SO₂Me |
| 3-12 | Me | 2-Oxolanylmethoxymethyl | SO₂Me |
| 3-13 | Cl | CO₂Me | SO₂Et |
| 3-14 | Cl | C(O)SMe | SO₂Me |
| 3-15 | Cl | C(O)SEt | SO₂Me |
| 3-16 | Me | OMe | SO₂Me |
| 3-17 | Me | OEt | SO₂Me |
| 3-18 | Me | O(i-Pr) | SO₂Me |
| 3-19 | Me | OCHF₂ | SO₂Me |
| 3-20 | Me | O(n-Pr) | SO₂Et |
| 3-21 | Cl | CH₂OMe | SO₂Me |
| 3-22 | Me | OCO₂Me | SO₂Me |
| 3-23 | Me | OC(O)SMe | SO₂Me |
| 3-24 | Me | OC(O)SEt | SO₂Me |
| 3-25 | Cl | CO₂(n-Pr) | SO₂Me |
| 3-26 | Me | CO₂Et | SO₂Me |
| 3-27 | Me | CH₂CO₂Me | SO₂Me |
| 3-28 | Me | OCH₂CO₂Et | SO₂Me |
| 3-29 | Me | O(n-Pr) | SO₂Me |
| 3-30 | Me | CH₂OCH₂CF₃ | SO₂Me |
| 3-31 | Cl | CH₂OCH₂CF₃ | SO₂Me |
| 3-32 | Me | Cl | SO₂Me |
| 3-33 | Me | CH₂SO₂Me | SO₂Me |
| 3-34 | Me | CH₂OEt | SO₂Me |
| 3-35 | Me | CH₂OMe | SO₂Me |
| 3-36 | Me | CH₂OCH₂OMe | SO₂Me |
| 3-37 | Me | OCH₂CH₂OEt | SO₂Me |
| 3-38 | Me | OCH₂CH₂Cl | SO₂Me |
| 3-39 | Me | OCH₂CF₃ | SO₂Me |
| 3-40 | Me | CH₂OCH₂OMe | SO₂Me |
| 3-41 | Me | OCH₂CH₂SMe | SO₂Me |
| 3-42 | Me | CN | SO₂Me |
| 3-43 | Me | CH₂CN | SO₂Me |
| 3-44 | Br | CO₂Me | SO₂Me |
| 3-45 | Cl | OCH₂CH₂OCF₃ | SO₂Me |
| 3-46 | Me | OCH₂CH₂OCF₃ | SO₂Me |
| 3-47 | CF₃ | OCH₂CH₂OCF₃ | SO₂Me |
| 3-48 | Br | OCH₂CH₂OCF₃ | SO₂Me |
| 3-49 | SO₂Me | OCH₂CH₂OCF₃ | CF₃ |
| 3-50 | Cl | OCH₂CH₂OCHClF | SO₂Me |
| 3-51 | Me | OCH₂CH₂OCHClF | SO₂Me |
| 3-52 | CF₃ | OCH₂CH₂OCHClF | SO₂Me |
| 3-53 | Br | OCH₂CH₂OCHClF | SO₂Me |
| 3-54 | SO₂Me | OCH₂CH₂OCHClF | CF₃ |
| 3-55 | Cl | OCH₂CHFOCF₃ | SO₂Me |
| 3-56 | Me | OCH₂CHFOCF₃ | SO₂Me |
| 3-57 | Cl | OCH₂CHFOMe | SO₂Me |
| 3-58 | Me | OCH₂CHFOMe | SO₂Me |
| 3-59 | CF₃ | OCH₂CHFOMe | SO₂Me |
| 3-60 | Br | OCH₂CHFOMe | SO₂Me |
| 3-61 | SO₂Me | OCH₂CHFOMe | CF₃ |
| 3-62 | Cl | OCHFCH₂OCF₃ | SO₂Me |
| 3-63 | Cl | OCH₂CH₂OCF₂Cl | SO₂Me |
| 3-64 | Me | OCH₂CH₂OCF₂Cl | SO₂Me |
| 3-65 | CF₃ | OCH₂CH₂OCF₂Cl | SO₂Me |
| 3-66 | Br | OCH₂CH₂OCF₂Cl | SO₂Me |
| 3-67 | SO₂Me | OCH₂CH₂OCF₂Cl | CF₃ |
| 3-68 | Cl | SCH₂CH₂OCH₃ | SO₂Me |
| 3-69 | Me | SCH₂CH₂OCH₃ | SO₂Me |
| 3-70 | CF₃ | SCH₂CH₂OCH₃ | SO₂Me |
| 3-71 | Br | SCH₂CH₂OCH₃ | SO₂Me |

TABLE a3-continued

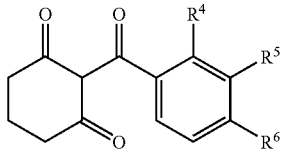

| No. | R⁴ | R⁵ | R⁶ |
|---|---|---|---|
| 3-72 | SO$_2$Me | SCH$_2$CH$_2$OCH$_3$ | CF$_3$ |
| 3-73 | Cl | SCH$_2$CH$_2$OCF$_3$ | SO$_2$Me |
| 3-74 | Me | SCH$_2$CH$_2$OCF$_3$ | SO$_2$Me |
| 3-75 | CF$_3$ | SCH$_2$CH$_2$OCF$_3$ | SO$_2$Me |
| 3-76 | Br | SCH$_2$CH$_2$OCF$_3$ | SO$_2$Me |
| 3-77 | SO$_2$Me | SCH$_2$CH$_2$OCF$_3$ | CF$_3$ |
| 3-78 | Cl | SCH$_2$CH$_2$SCH$_3$ | SO$_2$Me |
| 3-79 | Me | SCH$_2$CH$_2$SCH$_3$ | SO$_2$Me |
| 3-80 | CF$_3$ | SCH$_2$CH$_2$SCH$_3$ | SO$_2$Me |
| 3-81 | Br | SCH$_2$CH$_2$SCH$_3$ | SO$_2$Me |
| 3-82 | SO$_2$Me | SCH$_2$CH$_2$SCH$_3$ | CF$_3$ |
| 3-83 | Cl | SCH$_2$CH$_2$SCH$_3$ | SO$_2$Me |
| 3-84 | Me | SCH$_2$CH$_2$SCH$_3$ | SO$_2$Me |
| 3-85 | CF$_3$ | SCH$_2$CH$_2$SCH$_3$ | SO$_2$Me |
| 3-86 | Br | SCH$_2$CH$_2$SCH$_3$ | SO$_2$Me |
| 3-87 | SO$_2$Me | SCH$_2$CH$_2$SCH$_3$ | CF$_3$ |
| 3-88 | Cl | OCH$_2$CH(CH$_3$)OCH$_3$ | SO$_2$Me |
| 3-89 | Me | OCH$_2$CH(CH$_3$)OCH$_3$ | SO$_2$Me |
| 3-90 | CF$_3$ | OCH$_2$CH(CH$_3$)OCH$_3$ | SO$_2$Me |
| 3-91 | Br | OCH$_2$CH(CH$_3$)OCH$_3$ | SO$_2$Me |
| 3-92 | SO$_2$Me | OCH$_2$CH(CH$_3$)OCH$_3$ | CF$_3$ |
| 3-93 | Cl | OCH$_2$CF$_2$OCH$_3$ | SO$_2$Me |
| 3-94 | Me | OCH$_2$CF$_2$OCH$_3$ | SO$_2$Me |
| 3-95 | CF$_3$ | OCH$_2$CF$_2$OCH$_3$ | SO$_2$Me |
| 3-96 | Br | OCH$_2$CF$_2$OCH$_3$ | SO$_2$Me |
| 3-97 | SO$_2$Me | OCH$_2$CF$_2$OCH$_3$ | CF$_3$ |
| 3-98 | Me | OCH$_2$CF$_2$OCH$_3$ | SO$_2$Me |
| 3-99 | Me | OCH$_2$CH(OCH$_3$)$_2$ | SO$_2$Me |
| 3-100 | Me | CH$_2$N(Me)CH$_2$CN | SO$_2$Me |
| 3-101 | Me | (Tetrahydrofuran-2-yl)methoxy | SO$_2$Me |
| 3-102 | Cl | SMe | SO$_2$Me |
| 3-103 | Cl | Cl | SO$_2$Me |
| 3-104 | Cl | OMe | SO$_2$Me |
| 3-105 | Me | (Tetrahydro-2H-pyran-2-yl)methoxy | SO$_2$Me |
| 3-106 | Cl | OCH$_2$CH$_2$OMe | SO$_2$Me |
| 3-107 | Me | Tetrahydrofuran-3-yloxy | SO$_2$Me |
| 3-108 | Me | OCH$_2$CH$_2$OMe | SO$_2$Me |
| 3-109 | Cl | (1,3-Dioxolan-2-yl)ethoxy | SO$_2$Me |
| 3-110 | Me | Propargyloxy | SO$_2$Me |
| 3-111 | Me | (Tetrahydrofuran-3-yloxy)methyl | SO$_2$Me |
| 3-112 | Cl | SO$_2$Me | SO$_2$Me |
| 3-113 | Me | (CH$_2$)$_6$Me | SO$_2$Me |
| 3-114 | Me | CH$_2$CH$_2$CH$_2$OMe | SO$_2$Me |
| 3-115 | Cl | (1,3-Dioxolan-2-yl)methoxy | SO$_2$Me |
| 3-116 | Me | CH$_2$N[C(O)SEt]CH$_2$CN | SO$_2$Me |
| 3-117 | Me | CH=CHCN | SO$_2$Me |
| 3-118 | Me | CH$_2$CH$_2$CN | SO$_2$Me |
| 3-119 | Me | CH$_2$SCN | SO$_2$Me |
| 3-120 | Me | CH$_2$C(S)NH$_2$ | SO$_2$Me |
| 3-121 | Me | OCH(CH$_3$)CH$_2$OMe | SO$_2$Me |
| 3-122 | Me | OCH$_2$CH(Et)OMe | SO$_2$Me |
| 3-123 | Me | (1,3-Dioxolan-2-yl)methyl | SO$_2$Me |
| 3-124 | Me | CH$_2$O(i-Pr) | SO$_2$Me |
| 3-125 | Cl | (Tetrahydrofuran-2-yl)methoxymethyl | SO$_2$Me |

TABLE a4

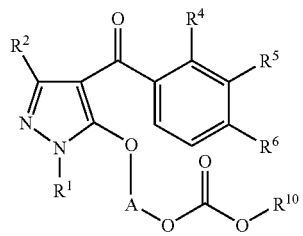

| No. | R¹ | R² | R¹⁰ | R⁴ | R⁵ | R⁶ | —A— |
|---|---|---|---|---|---|---|---|
| 4-1 | Me | H | Me | Me | OCH$_2$CH$_2$OMe | SO$_2$Me | —CH(Me)— |
| 4-2 | Me | H | Et | Me | OCH$_2$CH$_2$OMe | SO$_2$Me | —CH(Me)— |
| 4-3 | Et | H | Et | Me | OCH$_2$CH$_2$OMe | SO$_2$Me | —CH(Me)— |
| 4-4 | Me | H | i-Pr | Me | OCH$_2$CH$_2$OMe | SO$_2$Me | —CH(Me)— |
| 4-5 | Me | H | Et | Me | OCH$_2$CH$_2$OMe | SO$_2$Me | —C(Me)$_2$— |
| 4-6 | Me | H | Et | Me | OCH$_2$CF$_3$ | SO$_2$Me | —CH(Me)— |
| 4-7 | Me | H | Et | Me | CH$_2$OMe | SO$_2$Me | —CH(Me)— |
| 4-8 | Me | H | Et | Cl | CH$_2$OMe | SO$_2$Me | —CH(Me)— |
| 4-9 | n-Bu | H | Et | Me | OCH$_2$CH$_2$OMe | SO$_2$Me | —CH(Me)— |
| 4-10 | t-Bu | H | Et | Me | OCH$_2$CH$_2$OMe | SO$_2$Me | —CH(Me)— |
| 4-11 | Me | Me | Et | Me | OCH$_2$CH$_2$OMe | SO$_2$Me | —CH(Me)— |
| 4-12 | Me | H | Et | Me | OCH$_2$CH$_2$OMe | SO$_2$Me | —C(Me)(Et)— |
| 4-13 | Me | H | Et | Me | OCH$_2$CH$_2$OMe | SO$_2$Me | —CH(Et)— |
| 4-14 | Me | H | Et | Me | OCH$_2$CH$_2$OMe | SO$_2$Me | —CH(i-Pr)— |
| 4-15 | Me | H | Et | Me | CH$_2$OCH$_2$CF$_3$ | SO$_2$Me | —CH(Me)— |
| 4-16 | Et | H | Et | Cl | C(O)OMe | SO$_2$Me | —CH(Me)— |
| 4-17 | Me | H | Et | Cl | OCH$_2$CH$_2$OMe | SO$_2$Me | —CH(Me)— |
| 4-18 | i-Pr | H | Et | Me | OCH$_2$CH$_2$OMe | SO$_2$Me | —CH(Me)— |
| 4-19 | Me | H | n-Pr | Me | OCH$_2$CH$_2$OMe | SO$_2$Me | —CH(Me)— |
| 4-20 | Me | H | n-Bu | Me | OCH$_2$CH$_2$OMe | SO$_2$Me | —CH(Me)— |
| 4-21 | Me | H | Et | Me | C(O)OMe | SO$_2$Me | —CH(Me)— |

TABLE a4-continued

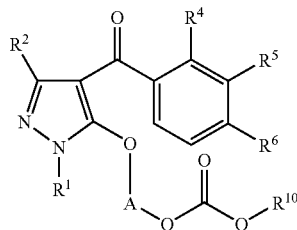

| No. | R¹ | R² | R¹⁰ | R⁴ | R⁵ | R⁶ | —A— |
|---|---|---|---|---|---|---|---|
| 4-22 | Me | H | Me | Me | OCH₂CH₂OMe | SO₂Me | —C(Me)₂— |
| 4-23 | Et | H | Et | Me | OCH₂CH₂OMe | SO₂Me | —C(Me)₂— |
| 4-24 | Me | H | i-Pr | Me | OCH₂CH₂OMe | SO₂Me | —C(Me)₂— |
| 4-25 | i-Pr | Me | Et | Me | OCH₂CH₂OMe | SO₂Me | —C(Me)₂— |
| 4-26 | Me | H | n-Pr | Me | OCH₂CH₂OMe | SO₂Me | —C(Me)₂— |
| 4-27 | Me | H | n-Bu | Me | OCH₂CH₂OMe | SO₂Me | —C(Me)₂— |
| 4-28 | Me | H | Et | Me | OCH₂CH₂OMe | SO₂Me | —C(Me)₂— |
| 4-29 | Et | H | Et | Cl | OCH₂CH₂OMe | SO₂Me | —CH(Me)— |
| 4-30 | t-Bu | H | Et | Cl | OCH₂CH₂OMe | SO₂Me | —CH(Me)— |
| 4-31 | Me | Me | Et | Cl | OCH₂CH₂OMe | SO₂Me | —CH(Me)— |
| 4-32 | Me | H | Me | Me | OCH₂CH₂OMe | SO₂Et | —CH(Me)— |
| 4-33 | Me | H | Et | Me | OCH₂CH₂OMe | SO₂Et | —CH(Me)— |
| 4-34 | Et | H | Et | Me | OCH₂CH₂OMe | SO₂Et | —CH(Me)— |
| 4-35 | Me | H | i-Pr | Me | OCH₂CH₂OMe | SO₂Et | —CH(Me)— |
| 4-36 | Me | H | Et | Me | OCH₂CH₂OMe | SO₂Et | —C(Me)₂— |
| 4-37 | Me | H | Et | Me | OCH₂CF₃ | SO₂Et | —CH(Me)— |
| 4-38 | Me | H | Et | Me | CH₂OMe | SO₂Et | —CH(Me)— |
| 4-39 | Me | H | Et | Cl | CH₂OMe | SO₂Et | —CH(Me)— |
| 4-40 | n-Bu | H | Et | Me | OCH₂CH₂OMe | SO₂Et | —CH(Me)— |
| 4-41 | t-Bu | H | Et | Me | OCH₂CH₂OMe | SO₂Et | —CH(Me)— |
| 4-42 | Me | Me | Et | Me | OCH₂CH₂OMe | SO₂Et | —CH(Me)— |
| 4-43 | Me | H | Et | Me | OCH₂CH₂OMe | SO₂Et | —C(Me)(Et)— |
| 4-44 | Me | H | Et | Me | OCH₂CH₂OMe | SO₂Et | —CH(Et)— |
| 4-45 | Me | H | Et | Me | OCH₂CH₂OMe | SO₂Et | —CH(i-Pr)— |
| 4-46 | Me | H | Et | Me | CH₂OCH₂CF₃ | SO₂Et | —CH(Me)— |
| 4-47 | Et | H | Et | Cl | C(O)OMe | SO₂Et | —CH(Me)— |
| 4-48 | Me | H | Et | Cl | OCH₂CH₂OMe | SO₂Et | —CH(Me)— |
| 4-49 | i-Pr | Me | Et | Me | OCH₂CH₂OMe | SO₂Et | —CH(Me)— |
| 4-50 | Me | H | n-Pr | Me | OCH₂CH₂OMe | SO₂Et | —CH(Me)— |
| 4-51 | Me | H | n-Bu | Me | OCH₂CH₂OMe | SO₂Et | —CH(Me)— |
| 4-52 | Me | H | Et | Me | C(O)OMe | SO₂Et | —CH(Me)— |
| 4-53 | Me | H | Me | Me | OCH₂CH₂OMe | SO₂Et | —C(Me)₂— |
| 4-54 | Et | H | Et | Me | OCH₂CH₂OMe | SO₂Et | —C(Me)₂— |
| 4-55 | Me | H | i-Pr | Me | OCH₂CH₂OMe | SO₂Et | —C(Me)₂— |
| 4-56 | Me | H | Me | Br | OCH₂CH₂OMe | SO₂Me | —CH(Me)— |
| 4-57 | Me | H | Et | Br | OCH₂CH₂OMe | SO₂Me | —CH(Me)— |
| 4-58 | Et | H | Et | Br | OCH₂CH₂OMe | SO₂Me | —CH(Me)— |
| 4-59 | Me | H | i-Pr | Br | OCH₂CH₂OMe | SO₂Me | —CH(Me)— |
| 4-60 | Me | H | Et | Br | OCH₂CH₂OMe | SO₂Me | —C(Me)₂— |
| 4-61 | Me | H | Et | Br | OCH₂CF₃ | SO₂Me | —CH(Me)— |
| 4-62 | Me | H | Et | Br | CH₂OMe | SO₂Me | —CH(Me)— |
| 4-63 | n-Bu | H | Et | Me | OCH₂CH₂OMe | SO₂Et | —CH(Me)— |
| 4-64 | t-Bu | H | i-Pr | Me | OCH₂CH₂OMe | SO₂Et | —CH(Me)— |
| 4-65 | Me | Me | i-Pr | Me | OCH₂CH₂OMe | SO₂Me | —CH(Me)— |
| 4-66 | Me | Et | Me | Me | OCH₂CH₂OMe | SO₂Me | —CH(Me)— |
| 4-67 | Me | Et | Et | Me | OCH₂CH₂OMe | SO₂Me | —CH(Me)— |
| 4-68 | Me | Et | i-Pr | Me | OCH₂CH₂OMe | SO₂Me | —CH(Me)— |
| 4-69 | Me | Et | n-Pr | Me | OCH₂CH₂OMe | SO₂Me | —CH(Me)— |
| 4-70 | Me | Et | n-Bu | Me | OCH₂CH₂OMe | SO₂Me | —CH(Me)— |
| 4-71 | Et | Et | Me | Me | OCH₂CH₂OMe | SO₂Me | —CH(Me)— |
| 4-72 | Et | Et | Et | Me | OCH₂CH₂OMe | SO₂Me | —CH(Me)— |
| 4-73 | Et | Et | i-Pr | Me | OCH₂CH₂OMe | SO₂Me | —CH(Me)— |
| 4-74 | Et | Et | n-Pr | Me | OCH₂CH₂OMe | SO₂Me | —CH(Me)— |
| 4-75 | Et | Et | n-Bu | Me | OCH₂CH₂OMe | SO₂Me | —CH(Me)— |
| 4-76 | i-Pr | Et | Me | Me | OCH₂CH₂OMe | SO₂Me | —CH(Me)— |
| 4-77 | i-Pr | Et | Et | Me | OCH₂CH₂OMe | SO₂Me | —CH(Me)— |
| 4-78 | i-Pr | Et | i-Pr | Me | OCH₂CH₂OMe | SO₂Me | —CH(Me)— |
| 4-79 | i-Pr | Et | n-Pr | Me | OCH₂CH₂OMe | SO₂Me | —CH(Me)— |
| 4-80 | i-Pr | Et | n-Bu | Me | OCH₂CH₂OMe | SO₂Me | —CH(Me)— |
| 4-81 | n-Pr | Et | Me | Me | OCH₂CH₂OMe | SO₂Me | —CH(Me)— |
| 4-82 | n-Pr | Et | Et | Me | OCH₂CH₂OMe | SO₂Me | —CH(Me)— |
| 4-83 | n-Pr | Et | i-Pr | Me | OCH₂CH₂OMe | SO₂Me | —CH(Me)— |
| 4-84 | n-Pr | Et | n-Pr | Me | OCH₂CH₂OMe | SO₂Me | —CH(Me)— |
| 4-85 | n-Pr | Et | n-Bu | Me | OCH₂CH₂OMe | SO₂Me | —CH(Me)— |
| 4-86 | n-Bu | Et | Me | Me | OCH₂CH₂OMe | SO₂Me | —CH(Me)— |

TABLE a4-continued

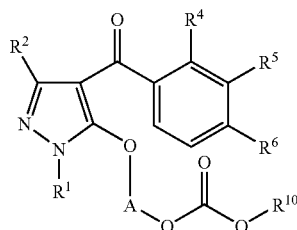

| No. | $R^1$ | $R^2$ | $R^{10}$ | $R^4$ | $R^5$ | $R^6$ | —A— |
|---|---|---|---|---|---|---|---|
| 4-87 | n-Bu | Et | Et | Me | OCH$_2$CH$_2$OMe | SO$_2$Me | —CH(Me)— |
| 4-88 | n-Bu | Et | i-Pr | Me | OCH$_2$CH$_2$OMe | SO$_2$Me | —CH(Me)— |
| 4-89 | n-Bu | Et | n-Pr | Me | OCH$_2$CH$_2$OMe | SO$_2$Me | —CH(Me)— |
| 4-90 | n-Bu | Et | n-Bu | Me | OCH$_2$CH$_2$OMe | SO$_2$Me | —CH(Me)— |
| 4-91 | t-Bu | Et | Me | Me | OCH$_2$CH$_2$OMe | SO$_2$Me | —CH(Me)— |
| 4-92 | t-Bu | Et | Et | Me | OCH$_2$CH$_2$OMe | SO$_2$Me | —CH(Me)— |
| 4-93 | t-Bu | Et | i-Pr | Me | OCH$_2$CH$_2$OMe | SO$_2$Me | —CH(Me)— |
| 4-94 | t-Bu | Et | n-Pr | Me | OCH$_2$CH$_2$OMe | SO$_2$Me | —CH(Me)— |
| 4-95 | t-Bu | Et | n-Bu | Me | OCH$_2$CH$_2$OMe | SO$_2$Me | —CH(Me)— |
| 4-96 | Me | Et | Me | Cl | OCH$_2$CH$_2$OMe | SO$_2$Me | —CH(Me)— |
| 4-97 | Me | Et | Et | Cl | OCH$_2$CH$_2$OMe | SO$_2$Me | —CH(Me)— |
| 4-98 | Me | Et | i-Pr | Cl | OCH$_2$CH$_2$OMe | SO$_2$Me | —CH(Me)— |
| 4-99 | Me | Et | n-Pr | Cl | OCH$_2$CH$_2$OMe | SO$_2$Me | —CH(Me)— |
| 4-100 | Me | Et | n-Bu | Cl | OCH$_2$CH$_2$OMe | SO$_2$Me | —CH(Me)— |
| 4-101 | Et | Et | Me | Cl | OCH$_2$CH$_2$OMe | SO$_2$Me | —CH(Me)— |
| 4-102 | Et | Et | Et | Cl | OCH$_2$CH$_2$OMe | SO$_2$Me | —CH(Me)— |
| 4-103 | Et | Et | i-Pr | Cl | OCH$_2$CH$_2$OMe | SO$_2$Me | —CH(Me)— |
| 4-104 | Et | Et | n-Pr | Cl | OCH$_2$CH$_2$OMe | SO$_2$Me | —CH(Me)— |
| 4-105 | Et | Et | n-Bu | Cl | OCH$_2$CH$_2$OMe | SO$_2$Me | —CH(Me)— |
| 4-106 | i-Pr | Et | Me | Cl | OCH$_2$CH$_2$OMe | SO$_2$Me | —CH(Me)— |
| 4-107 | i-Pr | Et | Et | Cl | OCH$_2$CH$_2$OMe | SO$_2$Me | —CH(Me)— |
| 4-108 | i-Pr | Et | i-Pr | Cl | OCH$_2$CH$_2$OMe | SO$_2$Me | —CH(Me)— |
| 4-109 | i-Pr | Et | n-Pr | Cl | OCH$_2$CH$_2$OMe | SO$_2$Me | —CH(Me)— |
| 4-110 | i-Pr | Et | n-Bu | Cl | OCH$_2$CH$_2$OMe | SO$_2$Me | —CH(Me)— |
| 4-111 | n-Pr | Et | Me | Cl | OCH$_2$CH$_2$OMe | SO$_2$Me | —CH(Me)— |
| 4-112 | n-Pr | Et | Et | Cl | OCH$_2$CH$_2$OMe | SO$_2$Me | —CH(Me)— |
| 4-113 | n-Pr | Et | i-Pr | Cl | OCH$_2$CH$_2$OMe | SO$_2$Me | —CH(Me)— |
| 4-114 | n-Pr | Et | n-Pr | Cl | OCH$_2$CH$_2$OMe | SO$_2$Me | —CH(Me)— |
| 4-115 | n-Pr | Et | n-Bu | Cl | OCH$_2$CH$_2$OMe | SO$_2$Me | —CH(Me)— |
| 4-116 | n-Bu | Et | Me | Cl | OCH$_2$CH$_2$OMe | SO$_2$Me | —CH(Me)— |
| 4-117 | n-Bu | Et | Et | Cl | OCH$_2$CH$_2$OMe | SO$_2$Me | —CH(Me)— |
| 4-118 | n-Bu | Et | i-Pr | Cl | OCH$_2$CH$_2$OMe | SO$_2$Me | —CH(Me)— |
| 4-119 | n-Bu | Et | n-Pr | Cl | OCH$_2$CH$_2$OMe | SO$_2$Me | —CH(Me)— |
| 4-120 | n-Bu | Et | n-Bu | Cl | OCH$_2$CH$_2$OMe | SO$_2$Me | —CH(Me)— |
| 4-121 | t-Bu | Et | Me | Cl | OCH$_2$CH$_2$OMe | SO$_2$Me | —CH(Me)— |
| 4-122 | t-Bu | Et | Et | Cl | OCH$_2$CH$_2$OMe | SO$_2$Me | —CH(Me)— |
| 4-123 | t-Bu | Et | i-Pr | Cl | OCH$_2$CH$_2$OMe | SO$_2$Me | —CH(Me)— |
| 4-124 | t-Bu | Et | n-Pr | Cl | OCH$_2$CH$_2$OMe | SO$_2$Me | —CH(Me)— |
| 4-125 | t-Bu | Et | n-Bu | Cl | OCH$_2$CH$_2$OMe | SO$_2$Me | —CH(Me)— |
| 4-126 | Me | Et | Me | Me | OCH$_2$CF$_3$ | SO$_2$Me | —CH(Me)— |
| 4-127 | Me | Et | Et | Me | OCH$_2$CF$_3$ | SO$_2$Me | —CH(Me)— |
| 4-128 | Me | Et | i-Pr | Me | OCH$_2$CF$_3$ | SO$_2$Me | —CH(Me)— |
| 4-129 | Me | Et | n-Pr | Me | OCH$_2$CF$_3$ | SO$_2$Me | —CH(Me)— |
| 4-130 | Me | Et | n-Bu | Me | OCH$_2$CF$_3$ | SO$_2$Me | —CH(Me)— |
| 4-131 | Et | Et | Me | Me | OCH$_2$CF$_3$ | SO$_2$Me | —CH(Me)— |
| 4-132 | Et | Et | Et | Me | OCH$_2$CF$_3$ | SO$_2$Me | —CH(Me)— |
| 4-133 | Et | Et | i-Pr | Me | OCH$_2$CF$_3$ | SO$_2$Me | —CH(Me)— |
| 4-134 | Et | Et | n-Pr | Me | OCH$_2$CF$_3$ | SO$_2$Me | —CH(Me)— |
| 4-135 | Et | Et | n-Bu | Me | OCH$_2$CF$_3$ | SO$_2$Me | —CH(Me)— |
| 4-136 | i-Pr | Et | Me | Me | OCH$_2$CF$_3$ | SO$_2$Me | —CH(Me)— |
| 4-137 | i-Pr | Et | Et | Me | OCH$_2$CF$_3$ | SO$_2$Me | —CH(Me)— |
| 4-138 | i-Pr | Et | i-Pr | Me | OCH$_2$CF$_3$ | SO$_2$Me | —CH(Me)— |
| 4-139 | i-Pr | Et | n-Pr | Me | OCH$_2$CF$_3$ | SO$_2$Me | —CH(Me)— |
| 4-140 | i-Pr | Et | n-Bu | Me | OCH$_2$CF$_3$ | SO$_2$Me | —CH(Me)— |
| 4-141 | n-Pr | Et | Me | Me | OCH$_2$CF$_3$ | SO$_2$Me | —CH(Me)— |
| 4-142 | n-Pr | Et | Et | Me | OCH$_2$CF$_3$ | SO$_2$Me | —CH(Me)— |
| 4-143 | n-Pr | Et | i-Pr | Me | OCH$_2$CF$_3$ | SO$_2$Me | —CH(Me)— |
| 4-144 | n-Pr | Et | n-Pr | Me | OCH$_2$CF$_3$ | SO$_2$Me | —CH(Me)— |
| 4-145 | n-Pr | Et | n-Bu | Me | OCH$_2$CF$_3$ | SO$_2$Me | —CH(Me)— |
| 4-146 | n-Bu | Et | Me | Me | OCH$_2$CF$_3$ | SO$_2$Me | —CH(Me)— |
| 4-147 | n-Bu | Et | Et | Me | OCH$_2$CF$_3$ | SO$_2$Me | —CH(Me)— |
| 4-148 | n-Bu | Et | i-Pr | Me | OCH$_2$CF$_3$ | SO$_2$Me | —CH(Me)— |
| 4-149 | n-Bu | Et | n-Pr | Me | OCH$_2$CF$_3$ | SO$_2$Me | —CH(Me)— |
| 4-150 | n-Bu | Et | n-Bu | Me | OCH$_2$CF$_3$ | SO$_2$Me | —CH(Me)— |
| 4-151 | t-Bu | Et | Me | Me | OCH$_2$CF$_3$ | SO$_2$Me | —CH(Me)— |

TABLE a4-continued

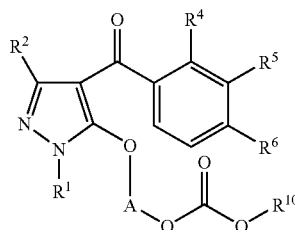

| No. | R¹ | R² | R¹⁰ | R⁴ | R⁵ | R⁶ | —A— |
|---|---|---|---|---|---|---|---|
| 4-152 | t-Bu | Et | Et | Me | OCH$_2$CF$_3$ | SO$_2$Me | —CH(Me)— |
| 4-153 | t-Bu | Et | i-Pr | Me | OCH$_2$CF$_3$ | SO$_2$Me | —CH(Me)— |
| 4-154 | t-Bu | Et | n-Pr | Me | OCH$_2$CF$_3$ | SO$_2$Me | —CH(Me)— |
| 4-155 | t-Bu | Et | n-Bu | Me | OCH$_2$CF$_3$ | SO$_2$Me | —CH(Me)— |
| 4-156 | Me | Et | Me | Cl | OCH$_2$CF$_3$ | SO$_2$Me | —CH(Me)— |
| 4-157 | Me | Et | Et | Cl | OCH$_2$CF$_3$ | SO$_2$Me | —CH(Me)— |
| 4-158 | Me | Et | i-Pr | Cl | OCH$_2$CF$_3$ | SO$_2$Me | —CH(Me)— |
| 4-159 | Me | Et | n-Pr | Cl | OCH$_2$CF$_3$ | SO$_2$Me | —CH(Me)— |
| 4-160 | Me | Et | n-Bu | Cl | OCH$_2$CF$_3$ | SO$_2$Me | —CH(Me)— |
| 4-161 | Et | Et | Me | Cl | OCH$_2$CF$_3$ | SO$_2$Me | —CH(Me)— |
| 4-162 | Et | Et | Et | Cl | OCH$_2$CF$_3$ | SO$_2$Me | —CH(Me)— |
| 4-163 | Et | Et | i-Pr | Cl | OCH$_2$CF$_3$ | SO$_2$Me | —CH(Me)— |
| 4-164 | Et | Et | n-Pr | Cl | OCH$_2$CF$_3$ | SO$_2$Me | —CH(Me)— |
| 4-165 | Et | Et | n-Bu | Cl | OCH$_2$CF$_3$ | SO$_2$Me | —CH(Me)— |
| 4-166 | i-Pr | Et | Me | Cl | OCH$_2$CF$_3$ | SO$_2$Me | —CH(Me)— |
| 4-167 | i-Pr | Et | Et | Cl | OCH$_2$CF$_3$ | SO$_2$Me | —CH(Me)— |
| 4-168 | i-Pr | Et | i-Pr | Cl | OCH$_2$CF$_3$ | SO$_2$Me | —CH(Me)— |
| 4-169 | i-Pr | Et | n-Pr | Cl | OCH$_2$CF$_3$ | SO$_2$Me | —CH(Me)— |
| 4-170 | i-Pr | Et | n-Bu | Cl | OCH$_2$CF$_3$ | SO$_2$Me | —CH(Me)— |
| 4-171 | n-Pr | Et | Me | Cl | OCH$_2$CF$_3$ | SO$_2$Me | —CH(Me)— |
| 4-172 | n-Pr | Et | Et | Cl | OCH$_2$CF$_3$ | SO$_2$Me | —CH(Me)— |
| 4-173 | n-Pr | Et | i-Pr | Cl | OCH$_2$CF$_3$ | SO$_2$Me | —CH(Me)— |
| 4-174 | n-Pr | Et | n-Pr | Cl | OCH$_2$CF$_3$ | SO$_2$Me | —CH(Me)— |
| 4-175 | n-Pr | Et | n-Bu | Cl | OCH$_2$CF$_3$ | SO$_2$Me | —CH(Me)— |
| 4-176 | n-Bu | Et | Me | Cl | OCH$_2$CF$_3$ | SO$_2$Me | —CH(Me)— |
| 4-177 | n-Bu | Et | Et | Cl | OCH$_2$CF$_3$ | SO$_2$Me | —CH(Me)— |
| 4-178 | n-Bu | Et | i-Pr | Cl | OCH$_2$CF$_3$ | SO$_2$Me | —CH(Me)— |
| 4-179 | n-Bu | Et | n-Pr | Cl | OCH$_2$CF$_3$ | SO$_2$Me | —CH(Me)— |
| 4-180 | n-Bu | Et | n-Bu | Cl | OCH$_2$CF$_3$ | SO$_2$Me | —CH(Me)— |
| 4-181 | t-Bu | Et | Me | Cl | OCH$_2$CF$_3$ | SO$_2$Me | —CH(Me)— |
| 4-182 | t-Bu | Et | Et | Cl | OCH$_2$CF$_3$ | SO$_2$Me | —CH(Me)— |
| 4-183 | t-Bu | Et | i-Pr | Cl | OCH$_2$CF$_3$ | SO$_2$Me | —CH(Me)— |
| 4-184 | t-Bu | Et | n-Pr | Cl | OCH$_2$CF$_3$ | SO$_2$Me | —CH(Me)— |
| 4-185 | t-Bu | Et | n-Bu | Cl | OCH$_2$CF$_3$ | SO$_2$Me | —CH(Me)— |
| 4-186 | Me | Et | Me | Me | CH$_2$OMe | SO$_2$Me | —CH(Me)— |
| 4-187 | Me | Et | Et | Me | CH$_2$OMe | SO$_2$Me | —CH(Me)— |
| 4-188 | Me | Et | i-Pr | Me | CH$_2$OMe | SO$_2$Me | —CH(Me)— |
| 4-189 | Me | Et | n-Pr | Me | CH$_2$OMe | SO$_2$Me | —CH(Me)— |
| 4-190 | Me | Et | n-Bu | Me | CH$_2$OMe | SO$_2$Me | —CH(Me)— |
| 4-191 | Et | Et | Me | Me | CH$_2$OMe | SO$_2$Me | —CH(Me)— |
| 4-192 | Et | Et | Et | Me | CH$_2$OMe | SO$_2$Me | —CH(Me)— |
| 4-193 | Et | Et | i-Pr | Me | CH$_2$OMe | SO$_2$Me | —CH(Me)— |
| 4-194 | Et | Et | n-Pr | Me | CH$_2$OMe | SO$_2$Me | —CH(Me)— |
| 4-195 | Et | Et | n-Bu | Me | CH$_2$OMe | SO$_2$Me | —CH(Me)— |
| 4-196 | i-Pr | Et | Me | Me | CH$_2$OMe | SO$_2$Me | —CH(Me)— |
| 4-197 | i-Pr | Et | Et | Me | CH$_2$OMe | SO$_2$Me | —CH(Me)— |
| 4-198 | i-Pr | Et | i-Pr | Me | CH$_2$OMe | SO$_2$Me | —CH(Me)— |
| 4-199 | i-Pr | Et | n-Pr | Me | CH$_2$OMe | SO$_2$Me | —CH(Me)— |
| 4-200 | i-Pr | Et | n-Bu | Me | CH$_2$OMe | SO$_2$Me | —CH(Me)— |
| 4-201 | n-Pr | Et | Me | Me | CH$_2$OMe | SO$_2$Me | —CH(Me)— |
| 4-202 | n-Pr | Et | Et | Me | CH$_2$OMe | SO$_2$Me | —CH(Me)— |
| 4-203 | n-Pr | Et | i-Pr | Me | CH$_2$OMe | SO$_2$Me | —CH(Me)— |
| 4-204 | n-Pr | Et | n-Pr | Me | CH$_2$OMe | SO$_2$Me | —CH(Me)— |
| 4-205 | n-Pr | Et | n-Bu | Me | CH$_2$OMe | SO$_2$Me | —CH(Me)— |
| 4-206 | n-Bu | Et | Me | Me | CH$_2$OMe | SO$_2$Me | —CH(Me)— |
| 4-207 | n-Bu | Et | Et | Me | CH$_2$OMe | SO$_2$Me | —CH(Me)— |
| 4-208 | n-Bu | Et | i-Pr | Me | CH$_2$OMe | SO$_2$Me | —CH(Me)— |
| 4-209 | n-Bu | Et | n-Pr | Me | CH$_2$OMe | SO$_2$Me | —CH(Me)— |
| 4-210 | n-Bu | Et | n-Bu | Me | CH$_2$OMe | SO$_2$Me | —CH(Me)— |
| 4-211 | t-Bu | Et | Me | Me | CH$_2$OMe | SO$_2$Me | —CH(Me)— |
| 4-212 | t-Bu | Et | Et | Me | CH$_2$OMe | SO$_2$Me | —CH(Me)— |
| 4-213 | t-Bu | Et | i-Pr | Me | CH$_2$OMe | SO$_2$Me | —CH(Me)— |
| 4-214 | t-Bu | Et | n-Pr | Me | CH$_2$OMe | SO$_2$Me | —CH(Me)— |
| 4-215 | t-Bu | Et | n-Bu | Me | CH$_2$OMe | SO$_2$Me | —CH(Me)— |
| 4-216 | Me | Et | Me | Cl | CH$_2$OMe | SO$_2$Me | —CH(Me)— |

TABLE a4-continued

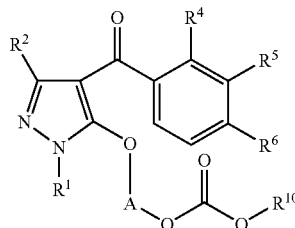

| No. | R¹ | R² | R¹⁰ | R⁴ | R⁵ | R⁶ | —A— |
|---|---|---|---|---|---|---|---|
| 4-217 | Me | Et | Et | Cl | $CH_2OMe$ | $SO_2Me$ | —CH(Me)— |
| 4-218 | Me | Et | i-Pr | Cl | $CH_2OMe$ | $SO_2Me$ | —CH(Me)— |
| 4-219 | Me | Et | n-Pr | Cl | $CH_2OMe$ | $SO_2Me$ | —CH(Me)— |
| 4-220 | Me | Et | n-Bu | Cl | $CH_2OMe$ | $SO_2Me$ | —CH(Me)— |
| 4-221 | Et | Et | Me | Cl | $CH_2OMe$ | $SO_2Me$ | —CH(Me)— |
| 4-222 | Et | Et | Et | Cl | $CH_2OMe$ | $SO_2Me$ | —CH(Me)— |
| 4-223 | Et | Et | i-Pr | Cl | $CH_2OMe$ | $SO_2Me$ | —CH(Me)— |
| 4-224 | Et | Et | n-Pr | Cl | $CH_2OMe$ | $SO_2Me$ | —CH(Me)— |
| 4-225 | Et | Et | n-Bu | Cl | $CH_2OMe$ | $SO_2Me$ | —CH(Me)— |
| 4-226 | i-Pr | Et | Me | Cl | $CH_2OMe$ | $SO_2Me$ | —CH(Me)— |
| 4-227 | i-Pr | Et | Et | Cl | $CH_2OMe$ | $SO_2Me$ | —CH(Me)— |
| 4-228 | i-Pr | Et | i-Pr | Cl | $CH_2OMe$ | $SO_2Me$ | —CH(Me)— |
| 4-229 | i-Pr | Et | n-Pr | Cl | $CH_2OMe$ | $SO_2Me$ | —CH(Me)— |
| 4-230 | i-Pr | Et | n-Bu | Cl | $CH_2OMe$ | $SO_2Me$ | —CH(Me)— |
| 4-231 | n-Pr | Et | Me | Cl | $CH_2OMe$ | $SO_2Me$ | —CH(Me)— |
| 4-232 | n-Pr | Et | Et | Cl | $CH_2OMe$ | $SO_2Me$ | —CH(Me)— |
| 4-233 | n-Pr | Et | i-Pr | Cl | $CH_2OMe$ | $SO_2Me$ | —CH(Me)— |
| 4-234 | n-Pr | Et | n-Pr | Cl | $CH_2OMe$ | $SO_2Me$ | —CH(Me)— |
| 4-235 | n-Pr | Et | n-Bu | Cl | $CH_2OMe$ | $SO_2Me$ | —CH(Me)— |
| 4-236 | n-Bu | Et | Me | Cl | $CH_2OMe$ | $SO_2Me$ | —CH(Me)— |
| 4-237 | n-Bu | Et | Et | Cl | $CH_2OMe$ | $SO_2Me$ | —CH(Me)— |
| 4-238 | n-Bu | Et | i-Pr | Cl | $CH_2OMe$ | $SO_2Me$ | —CH(Me)— |
| 4-239 | n-Bu | Et | n-Pr | Cl | $CH_2OMe$ | $SO_2Me$ | —CH(Me)— |
| 4-240 | n-Bu | Et | n-Bu | Cl | $CH_2OMe$ | $SO_2Me$ | —CH(Me)— |
| 4-241 | t-Bu | Et | Me | Cl | $CH_2OMe$ | $SO_2Me$ | —CH(Me)— |
| 4-242 | t-Bu | Et | Et | Cl | $CH_2OMe$ | $SO_2Me$ | —CH(Me)— |
| 4-243 | t-Bu | Et | i-Pr | Cl | $CH_2OMe$ | $SO_2Me$ | —CH(Me)— |
| 4-244 | t-Bu | Et | n-Pr | Cl | $CH_2OMe$ | $SO_2Me$ | —CH(Me)— |
| 4-245 | t-Bu | Et | n-Bu | Cl | $CH_2OMe$ | $SO_2Me$ | —CH(Me)— |
| 4-246 | Me | Et | Me | Me | C(O)OMe | $SO_2Me$ | —CH(Me)— |
| 4-247 | Me | Et | Et | Me | C(O)OMe | $SO_2Me$ | —CH(Me)— |
| 4-248 | Me | Et | i-Pr | Me | C(O)OMe | $SO_2Me$ | —CH(Me)— |
| 4-249 | Me | Et | n-Pr | Me | C(O)OMe | $SO_2Me$ | —CH(Me)— |
| 4-250 | Me | Et | n-Bu | Me | C(O)OMe | $SO_2Me$ | —CH(Me)— |
| 4-251 | Et | Et | Me | Me | C(O)OMe | $SO_2Me$ | —CH(Me)— |
| 4-252 | Et | Et | Et | Me | C(O)OMe | $SO_2Me$ | —CH(Me)— |
| 4-253 | Et | Et | i-Pr | Me | C(O)OMe | $SO_2Me$ | —CH(Me)— |
| 4-254 | Et | Et | n-Pr | Me | C(O)OMe | $SO_2Me$ | —CH(Me)— |
| 4-255 | Et | Et | n-Bu | Me | C(O)OMe | $SO_2Me$ | —CH(Me)— |
| 4-256 | i-Pr | Et | Me | Me | C(O)OMe | $SO_2Me$ | —CH(Me)— |
| 4-257 | i-Pr | Et | Et | Me | C(O)OMe | $SO_2Me$ | —CH(Me)— |
| 4-258 | i-Pr | Et | i-Pr | Me | C(O)OMe | $SO_2Me$ | —CH(Me)— |
| 4-259 | i-Pr | Et | n-Pr | Me | C(O)OMe | $SO_2Me$ | —CH(Me)— |
| 4-260 | i-Pr | Et | n-Bu | Me | C(O)OMe | $SO_2Me$ | —CH(Me)— |
| 4-261 | n-Pr | Et | Me | Me | C(O)OMe | $SO_2Me$ | —CH(Me)— |
| 4-262 | n-Pr | Et | Et | Me | C(O)OMe | $SO_2Me$ | —CH(Me)— |
| 4-263 | n-Pr | Et | i-Pr | Me | C(O)OMe | $SO_2Me$ | —CH(Me)— |
| 4-264 | n-Pr | Et | n-Pr | Me | C(O)OMe | $SO_2Me$ | —CH(Me)— |
| 4-265 | n-Pr | Et | n-Bu | Me | C(O)OMe | $SO_2Me$ | —CH(Me)— |
| 4-266 | n-Bu | Et | Me | Me | C(O)OMe | $SO_2Me$ | —CH(Me)— |
| 4-267 | n-Bu | Et | Et | Me | C(O)OMe | $SO_2Me$ | —CH(Me)— |
| 4-268 | n-Bu | Et | i-Pr | Me | C(O)OMe | $SO_2Me$ | —CH(Me)— |
| 4-269 | n-Bu | Et | n-Pr | Me | C(O)OMe | $SO_2Me$ | —CH(Me)— |
| 4-270 | n-Bu | Et | n-Bu | Me | C(O)OMe | $SO_2Me$ | —CH(Me)— |
| 4-271 | t-Bu | Et | Me | Me | C(O)OMe | $SO_2Me$ | —CH(Me)— |
| 4-272 | t-Bu | Et | Et | Me | C(O)OMe | $SO_2Me$ | —CH(Me)— |
| 4-273 | t-Bu | Et | i-Pr | Me | C(O)OMe | $SO_2Me$ | —CH(Me)— |
| 4-274 | t-Bu | Et | n-Pr | Me | C(O)OMe | $SO_2Me$ | —CH(Me)— |
| 4-275 | t-Bu | Et | n-Bu | Me | C(O)OMe | $SO_2Me$ | —CH(Me)— |
| 4-276 | Me | Et | Me | Cl | C(O)OMe | $SO_2Me$ | —CH(Me)— |
| 4-277 | Me | Et | Et | Cl | C(O)OMe | $SO_2Me$ | —CH(Me)— |
| 4-278 | Me | Et | i-Pr | Cl | C(O)OMe | $SO_2Me$ | —CH(Me)— |
| 4-279 | Me | Et | n-Pr | Cl | C(O)OMe | $SO_2Me$ | —CH(Me)— |
| 4-280 | Me | Et | n-Bu | Cl | C(O)OMe | $SO_2Me$ | —CH(Me)— |
| 4-281 | Et | Et | Me | Cl | C(O)OMe | $SO_2Me$ | —CH(Me)— |

TABLE a4-continued

| No. | R¹ | R² | R¹⁰ | R⁴ | R⁵ | R⁶ | —A— |
|---|---|---|---|---|---|---|---|
| 4-282 | Et | Et | Et | Cl | C(O)OMe | SO₂Me | —CH(Me)— |
| 4-283 | Et | Et | i-Pr | Cl | C(O)OMe | SO₂Me | —CH(Me)— |
| 4-284 | Et | Et | n-Pr | Cl | C(O)OMe | SO₂Me | —CH(Me)— |
| 4-285 | Et | Et | n-Bu | Cl | C(O)OMe | SO₂Me | —CH(Me)— |
| 4-286 | i-Pr | Et | Me | Cl | C(O)OMe | SO₂Me | —CH(Me)— |
| 4-287 | i-Pr | Et | Et | Cl | C(O)OMe | SO₂Me | —CH(Me)— |
| 4-288 | i-Pr | Et | i-Pr | Cl | C(O)OMe | SO₂Me | —CH(Me)— |
| 4-289 | i-Pr | Et | n-Pr | Cl | C(O)OMe | SO₂Me | —CH(Me)— |
| 4-290 | i-Pr | Et | n-Bu | Cl | C(O)OMe | SO₂Me | —CH(Me)— |
| 4-291 | n-Pr | Et | Me | Cl | C(O)OMe | SO₂Me | —CH(Me)— |
| 4-292 | n-Pr | Et | Et | Cl | C(O)OMe | SO₂Me | —CH(Me)— |
| 4-293 | n-Pr | Et | i-Pr | Cl | C(O)OMe | SO₂Me | —CH(Me)— |
| 4-294 | n-Pr | Et | n-Pr | Cl | C(O)OMe | SO₂Me | —CH(Me)— |
| 4-295 | n-Pr | Et | n-Bu | Cl | C(O)OMe | SO₂Me | —CH(Me)— |
| 4-296 | n-Bu | Et | Me | Cl | C(O)OMe | SO₂Me | —CH(Me)— |
| 4-297 | n-Bu | Et | Et | Cl | C(O)OMe | SO₂Me | —CH(Me)— |
| 4-298 | n-Bu | Et | i-Pr | Cl | C(O)OMe | SO₂Me | —CH(Me)— |
| 4-299 | n-Bu | Et | n-Pr | Cl | C(O)OMe | SO₂Me | —CH(Me)— |
| 4-300 | n-Bu | Et | n-Bu | Cl | C(O)OMe | SO₂Me | —CH(Me)— |
| 4-301 | t-Bu | Et | Me | Cl | C(O)OMe | SO₂Me | —CH(Me)— |
| 4-302 | t-Bu | Et | Et | Cl | C(O)OMe | SO₂Me | —CH(Me)— |
| 4-303 | t-Bu | Et | i-Pr | Cl | C(O)OMe | SO₂Me | —CH(Me)— |
| 4-304 | t-Bu | Et | n-Pr | Cl | C(O)OMe | SO₂Me | —CH(Me)— |
| 4-305 | t-Bu | Et | n-Bu | Cl | C(O)OMe | SO₂Me | —CH(Me)— |
| 4-306 | Me | H | Et | Me | CH₂OCH(Me)₂ | SO₂Me | —CH(Me)— |
| 4-307 | Et | H | Et | Me | CH₂OCH(Me)₂ | SO₂Me | —CH(Me)— |
| 4-308 | n-Pr | H | Et | Me | CH₂OCH(Me)₂ | SO₂Me | —CH(Me)— |
| 4-309 | i-Pr | H | Et | Me | CH₂OCH(Me)₂ | SO₂Me | —CH(Me)— |
| 4-310 | Me | H | Et | Cl | CH₂OCH(Me)₂ | SO₂Me | —CH(Me)— |
| 4-311 | Et | H | Et | Cl | CH₂OCH(Me)₂ | SO₂Me | —CH(Me)— |
| 4-312 | n-Pr | H | Et | Cl | CH₂OCH(Me)₂ | SO₂Me | —CH(Me)— |
| 4-313 | i-Pr | H | Et | Cl | CH₂OCH(Me)₂ | SO₂Me | —CH(Me)— |
| 4-314 | Me | H | Me | Me | CH₂OEt | SO₂Me | —CH(Me)— |
| 4-315 | Me | H | Me | Me | C(O)OMe | SO₂Me | —CH(Me)— |
| 4-316 | Me | H | Me | Me | CH₂OMe | SO₂Me | —CH(Me)— |
| 4-317 | Me | H | Et | Me | CH₂OEt | SO₂Me | —CH(Me)— |
| 4-318 | Me | H | Et | Me | OCH₂CH₂OCH(Me)₂ | SO₂Me | —CH(Me)— |
| 4-319 | Me | Me | Me | Me | OCH₂CH₂OMe | SO₂Me | —CH(Me)— |
| 4-320 | Et | H | Me | Me | OCH₂CH₂OMe | SO₂Me | —CH(Me)— |
| 4-321 | Et | H | Et | Me | C(O)OMe | SO₂Me | —CH(Me)— |
| 4-322 | Et | Me | Et | Me | OCH₂CH₂OMe | SO₂Me | —CH(Me)— |
| 4-323 | n-Pr | H | Et | Me | OCH₂CH₂OMe | SO₂Me | —CH(Me)— |
| 4-324 | i-Pr | H | Me | Me | OCH₂CH₂OMe | SO₂Me | —CH(Me)— |

TABLE a5

| No. | R¹¹ | R¹² |
|---|---|---|
| 5-1 | CH₂OCH₂CH₂OMe | CF₃ |

In the present invention, the mix ratio of (1) the compound of the formula (I) or its salt to (2) the POA alkyl ether phosphate or its salt cannot generally be defined, since it is suitably changed depending upon the types of the compound of the formula (I) or its salt, and the POA alkyl ether phosphate or its salt, the types of the formulations, weather conditions, the type or the size of plants to be controlled, etc. However, the mix ratio may, for example, be within a range of from 10:1 to 1:10,000, preferably from 5:1 to 1:3,000, more preferably from 3:1 to 1:300, particularly preferably from 1:1 to 1:30 by weight ratio of (1):(2).

In the present invention, in a case where (3) an oil such as a vegetable oil, a fatty acid ester or a hydrocarbon solvent is further used as a coadjuvant, the mix ratio of (2) the POA alkyl ether phosphate or its salt to (3) the oil cannot generally be defined since it is suitably changed depending upon the types of the compound of the formula (I) or its salt, and the POA alkyl ether phosphate or its salt, the types of the formulations, weather conditions, the type or the size of plants to be controlled, etc. However, the mix ratio may, for example, be within a range of from 100:1 to 1:100, preferably from 50:1 to 1:50, more preferably from 10:1 to 1:10, by weight ratio of (2):(3).

In the present invention, in a case where (3) the above oil is used, (4) an emulsifying agent may be used as the case requires. The mix ratio of the oil to the emulsifying agent cannot generally be defined since it is suitably changed depending upon the types of the compound of the formula (I) or its salt, the POA alkyl ether phosphate or its salt, and the oil, the types of the formulations, weather conditions, the type or the size of plants to be controlled, etc. However, the mix ratio may, for example, be within a range of from 100:1 to 1:100, preferably from 50:1 to 1:50, more preferably from 10:1 to 1:10, by weight ratio of (3):(4).

Further, in a case where the compound of the formula (I) or its salt is formulated by using various additives, the obtained formulation is diluted with e.g. water together with the POA alkyl ether phosphate or its salt, and the diluted liquid is applied to undesired plants or to a place where they grow, the compound of the formula (I) or its salt is applied as diluted with from 30 to 5,000 L/ha, preferably from 50 to 2,000 L/ha, of water containing the POA alkyl ether phosphate or its salt in a proportion of from 0.005 to 4 vol %, preferably from 0.01 to 2 vol %.

Further, in a case where the oil or the emulsifying agent is used, the compound of the formula (I) or its salt may be applied as diluted with from 30 to 5,000 L/ha, preferably from 50 to 2,000 L/ha, of water containing the oil in a proportion of from 0.005 to 4 vol %, preferably from 0.01 to 2 vol %, or the emulsifying agent in a proportion of from 0.005 to 4 vol %, preferably from 0.01 to 2 vol %, together with the POA alkyl ether phosphate or its salt in the above proportion.

Now, some preferred embodiments of the present invention will be described. However, the present invention is by no means thereby restricted.

(i) A herbicidal composition comprising (1) the compound of the formula (I) or its salt, (2) a polyoxyalkylene alkyl ether phosphate or its salt, and (3) at least one oil selected from the group consisting of a vegetable oil, a fatty acid ester and a hydrocarbon solvent.

(ii) A herbicidal composition comprising (1) the compound of the formula (I) or its salt, (2) a polyoxyalkylene alkyl ether phosphate or its salt, and (3) at least one oil selected from the group consisting of a vegetable oil, a fatty acid ester and a hydrocarbon solvent, and (4) an emulsifying agent.

(iii) A method for improving the herbicidal effect of (1) the compound of the formula (I) or its salt by using (2) a polyoxyalkylene alkyl ether phosphate or its salt.

(iv) A method for improving the herbicidal effect of (1) the compound of the formula (I) or its salt by using (2) a polyoxyalkylene alkyl ether phosphate or its salt, and (3) at least one oil selected from the group consisting of a vegetable oil, a fatty acid ester and a hydrocarbon solvent.

(v) A method for improving the herbicidal effect of (1) the compound of the formula (I) or its salt by using (2) a polyoxyalkylene alkyl ether phosphate or its salt, (3) at least one oil selected from the group consisting of a vegetable oil, a fatty acid ester and a hydrocarbon solvent, and (4) an emulsifying agent.

(vi) A method for controlling undesired plants, which comprises applying the above herbicidal composition to the undesired plants or to a place where they grow.

(vii) A method for controlling undesired plants, which comprises applying (1) the compound of the formula (I) or its salt and (2) a polyoxyalkylene alkyl ether phosphate or its salt to the undesired plants or to a place where they grow.

(viii) A herbicidal composition comprising (1) the compound of the formula (I) or its salt, wherein T is $T^1$, Q is hydrogen, $R^1$ is alkyl, $R^2$ is hydrogen, Z is $Z^1$, $R^4$ is alkyl, $R^5$ is alkoxyalkyl, alkoxy, alkoxyalkoxy or —C(O)$OR^7$, and $R^6$ is alkylsulfonyl, and (2) a polyoxyalkylene alkyl ether phosphate or its salt.

(ix) The herbicidal composition according to the above (viii) wherein in the formula (I), T is $T^1$, Q is hydrogen, $R^1$ is alkyl, $R^2$ is hydrogen, Z is $Z^1$, $R^4$ is alkyl, $R^5$ is alkoxyalkyl, and $R^6$ is alkylsulfonyl.

(x) The herbicidal composition according to the above (ix), wherein in the formula (I), T is $T^1$, Q is hydrogen, $R^1$ is methyl, $R^2$ is hydrogen, Z is $Z^1$, $R^4$ is methyl, $R^5$ is ethoxymethyl, and $R^6$ is methylsulfonyl.

(xi) The herbicidal composition according to the above (ix), wherein in the formula (I), T is $T^1$, Q is hydrogen, $R^1$ is methyl, $R^2$ is hydrogen, Z is $Z^1$, $R^4$ is methyl, $R^5$ is methoxymethyl, and $R^6$ is methylsulfonyl.

(xii) The herbicidal composition according to the above (viii), wherein in the formula (I), T is $T^1$, Q is hydrogen, $R^1$ is alkyl, $R^2$ is hydrogen, Z is $Z^1$, $R^4$ is alkyl, $R^5$ is alkoxy, and $R^6$ is alkylsulfonyl.

(xiii) The herbicidal composition according to the above (xii), wherein in the formula (I), T is $T^1$, Q is hydrogen, $R^1$ is methyl, $R^2$ is hydrogen, Z is $Z^1$, $R^4$ is methyl, $R^5$ is ethoxy, and $R^6$ is methylsulfonyl.

(xiv) The herbicidal composition according to the above (xii), wherein in the formula (I), T is $T^1$, Q is hydrogen, $R^1$ is methyl, $R^2$ is hydrogen, Z is $Z^1$, $R^4$ is methyl, $R^5$ is n-propoxy, and $R^6$ is methylsulfonyl.

(xv) The herbicidal composition according to the above (xii), wherein in the formula (I), T is $T^1$, Q is hydrogen, $R^1$ is methyl, $R^2$ is hydrogen, Z is $Z^1$, $R^4$ is methyl, $R^5$ is n-butyloxy, and $R^6$ is methylsulfonyl.

(xvi) The herbicidal composition according to the above (xii), wherein in the formula (I), T is $T^1$, Q is hydrogen, $R^1$ is methyl, $R^2$ is hydrogen, Z is $Z^1$, $R^4$ is methyl, $R^5$ is isobutyloxy, and $R^6$ is methylsulfonyl.

(xvii) The herbicidal composition according to the above (viii), wherein in the formula (I), T is $T^1$, Q is hydrogen, $R^1$ is alkyl, $R^2$ is hydrogen, Z is $Z^1$, $R^4$ is alkyl, $R^5$ is alkoxyalkoxy, and $R^6$ is alkylsulfonyl.

(xviii) The herbicidal composition according to the above (xvii), wherein in the formula (I), T is $T^1$, Q is hydrogen, $R^1$ is methyl, $R^2$ is hydrogen, Z is $Z^1$, $R^4$ is methyl, $R^5$ is 2-methoxyethoxy, and $R^6$ is methylsulfonyl.

(xix) The herbicidal composition according to the above (xvii), wherein in the formula (I), T is $T^1$, Q is hydrogen, $R^1$ is ethyl, $R^2$ is hydrogen, Z is $Z^1$, $R^4$ is methyl, $R^5$ is 2-methoxyethoxy, and $R^6$ is methylsulfonyl.

(xx) The herbicidal composition according to the above (viii), wherein in the formula (I), T is $T^1$, Q is hydrogen, $R^1$ is alkyl, $R^2$ is hydrogen, Z is $Z^1$, $R^4$ is alkyl, $R^5$ is —C(O)$OR^7$, and $R^6$ is alkylsulfonyl.

(xxi) The herbicidal composition according to the above (xx), wherein in the formula (I), T is $T^1$, Q is hydrogen, $R^1$ is methyl, $R^2$ is hydrogen, Z is $Z^1$, $R^4$ is methyl, $R^5$ is methoxycarbonyl, and $R^6$ is methylsulfonyl.

(xxii) A herbicidal composition comprising (1) a compound of the formula (I) or its salt, wherein T is $T^1$, Q is -A-O—C(O)$OR^{10}$, $R^1$ is alkyl, $R^2$ is hydrogen, Z is $Z^1$, $R^4$ is alkyl, $R^5$ is alkoxyalkyl, alkoxy, alkoxyalkoxy or —C(O)$OR^7$, $R^6$ is alkylsulfonyl, A is alkylene substituted by at least one alkyl, and $R^{10}$ is alkyl, and (2) a polyoxyalkylene alkyl ether phosphate or its salt.

(xxiii) The herbicidal composition according the above (xxii), wherein in the formula (I), T is $T^1$, Q is -A-O—C(O)

$OR^{16}$, $R^1$ is alkyl, $R^2$ is hydrogen, Z is $Z^1$, $R^4$ is alkyl, $R^5$ is alkoxyalkoxy, $R^6$ is alkylsulfonyl, A is alkylene substituted by at least one alkyl, and $R^{10}$ is alkyl.

(xxiv) The herbicidal composition according the above (xxiii), wherein in the formula (I), T is $T^1$, Q is —CH(CH$_3$)—O—C(O)OCH$_2$CH$_3$, $R^1$ is ethyl, $R^2$ is hydrogen, Z is $Z^1$, $R^4$ is methyl, $R^5$ is 2-methoxyethoxy, and $R^6$ is methylsulfonyl.

(xxv) The herbicidal composition according the above (xxiii), wherein in the formula (I), T is $T^1$, Q is —CH(CH$_3$)—O—C(O)OCH$_3$, $R^1$ is ethyl, $R^2$ is hydrogen, Z is $Z^1$, $R^4$ is methyl, $R^5$ is 2-methoxyethoxy, and $R^6$ is methylsulfonyl.

(xxvi) A herbicidal composition comprising (1) a compound of the formula (I) or its salt, wherein T is $T^2$, Z is $Z^1$, $R^4$ is halogen, $R^5$ is haloalkoxyalkyl, and $R^6$ is alkylsulfonyl, and (2) a polyoxyalkylene alkyl ether phosphate or its salt.

(xxvii) The herbicidal composition according to the above (xxvi), wherein in the formula (I), T is $T^2$, Z is $Z^1$, $R^4$ is chlorine, $R^5$ is —CH$_2$OCH$_2$CF$_3$, and $R^6$ is methylsulfonyl.

(xxviii) A herbicidal composition comprising (1) a compound of the formula (I) or its salt, wherein T is $T^3$, Z is $Z^2$, $R^{11}$ is alkoxyalkoxyalkyl, and $R^{12}$ is haloalkyl, and (2) a polyoxyalkylene alkyl ether phosphate or its salt.

(xxix) The herbicidal composition according to the above (xxviii), wherein in the formula (I), T is $T^3$, Z is $Z^2$, $R^{11}$ is —CH$_2$OCH$_2$CH$_2$OCH$_3$, and $R^{12}$ is trifluoromethyl.

EXAMPLES

Now, the present invention will be described with reference to Examples, but the present invention is by no means thereby restricted.

Example 1

1

| | | |
|---|---|---|
| (1) | Sodium dodecylbenzenesulfonate (tradename: Sorpol 5060, manufactured by TOHO Chemical Industry Co., Ltd.) | 2.0 parts by weight |
| (2) | Polyoxyethylene nonylphenyl ether sulfate (tradename: Sorpol 5073, manufactured by TOHO Chemical Industry Co., Ltd.) | 3.0 parts by weight |
| (3) | Polyoxyethylene dodecylphenyl ether (tradename: NOIGEN EA-33, manufactured by DAI-ICHI KOGYO SEIYAKU CO., LTD.) | 1.0 part by weight |
| (4) | Clay (tradename: OQ clay, manufactured by NIHON TAIKA GENRYO Co., Ltd.) | 78.0 parts by weight |
| (5) | White carbon (tradename: CARPLEX CS-7, manufactured by Shionogi & Co., Ltd.) | 16.0 parts by weight |

The above components are mixed to obtain a composition (A).

2

| | | |
|---|---|---|
| (1) | Compound No. 1 | 10.0 parts by weight |
| (2) | The above composition (A) | 90.0 parts by weight |

The above components were mixed to obtain a wettable powder. The wettable powder is diluted with water together with a surfactant (tradename: NIKKOL DDP-8) containing the POA alkyl ether phosphate, followed by applying.

Example 2

| | | |
|---|---|---|
| (1) | Compound No. 53 | 5.1 parts by weight |
| (2) | Potassium polyoxyethylene tristyryl phenyl ether phosphate (tradename: Soprophor FLK/70, manufactured by Rhodia Nicca, Ltd. | 3.0 parts by weight |
| (3) | Alkylnaphthalene sulfonic acid-formalin condensate (tradename: Morwet D425, manufactured by LION AKZO Co., Ltd. | 3.0 parts by weight |
| (4) | Propylene glycol | 10.0 parts by weight |
| (5) | Magnesium aluminum silicate (tradename: Veegum, manufactured by Sanyo Chemical Industries, Ltd.) | 1.0 part by weight |
| (6) | Polydimethylsiloxane (tradename: Rhodorsil 432, manufactured by Rhodia Nicca, Ltd.) | 0.1 part by weight |
| (7) | Xanthan gum (tradename: Rhodpol 23, manufactured by Rhodia Nicca, Ltd.) | 0.1 part by weight |
| (8) | 1,2-Dibenzisothiazolin-3-one (tradename: Proxel GXL, manufactured by Avecia Inc.) | 0.05 part by weight |
| (9) | Water | 77.65 parts by weight |

The above components were mixed and pulverized for 5 minutes by means of a wet system pulverizer to obtain a water-based suspension concentrate. This suspension concentrate was diluted with water together with NIKKOL DDP-8 (tradename), followed by applying.

Example 3

A water-based suspension concentrate was obtained in the same manner as in Example 2 except that compound No. 53 in Example 2 was changed to compound No. 238. This suspension concentrate was diluted with water together with a surfactant containing the POA alkyl ether phosphate (tradename: ADEKA COL PS-440E), a fatty acid ester (tradename: AGNIQUE Me 18RD-F, manufactured by Cognis Deutschland GmbH Co. & KG), a hydrocarbon solvent (tradename: Solvesso 150, manufactured by Exxon Chemical Company) and an emulsifying agent (a mixture of polyoxyethylene sorbitol tetraoleate, polyoxyethylene castor oil and calcium dodecyl benzenesulfonate), followed by applying.

Example 4

| | |
|---|---|
| (1) Compound No. 2-27 | 10.0 parts by weight |
| (2) Composition [A] in Example 1 | 90.0 parts by weight |

The above components were mixed to obtain a wettable powder. This wettable powder was diluted with water together with a surfactant (tradename: NIKKOL TDP-8) containing the POA alkyl ether phosphate, followed by applying.

Example 5

| | |
|---|---|
| (1) Compound No. 3-31 | 10.0 parts by weight |
| (2) Composition [A] in Example 1 | 90.0 parts by weight |

The above components were mixed to obtain a wettable powder. This wettable powder was diluted with water together with NIKKOL TDP-8 (tradename), followed by applying.

Example 6

| | | |
|---|---|---|
| (1) | Compound No. 238 | 5.1 parts by weight |
| (2) | Soprophor FLK/70 (tradename) | 3.0 parts by weight |
| (3) | Propylene glycol | 10.0 parts by weight |
| (4) | Veegum (tradename) | 1.0 part by weight |
| (5) | Rhodorsil 432 (tradename) | 0.1 part by weight |
| (6) | Rhodpol 23 (tradename) | 0.1 part by weight |
| (7) | Proxel GXL (tradename) | 0.05 part by weight |
| (8) | water | 80.65 parts by weight |

The above components were mixed and pulverized for 5 minutes by means of a wet system pulverizer to obtain a water-based suspension concentrate. This suspension concentrate was diluted with water together with NIKKOL TDP-8 (tradename), followed by applying.

Test Example 1

Upland field soil was put into a 1/1,000,000 ha pot, and seeds of crabgrass (*Digitaria sanguinalis* L.) and velvetleaf (*Abutilon theophrasti* L.) were respectively sown and grown in a greenhouse. When crabgrass reached 4.2 to 5.0 leaf stage and velvetleaf reached 3.5 to 4.3 leaf stage, a prescribed amount (15 g a.i./ha) of a wettable powder comprising compound No. 1 as an active ingredient, prepared in accordance with the above Example 1, was diluted with water corresponding to 300 L/ha (containing 0.05 vol % of a surfactant containing the POA alkyl ether phosphate), followed by foliar application (the present invention). Further, for comparison, foliar application was carried out in the same manner by using an alkylaryl polyglycol ether surfactant (tradename: CITOWETT) at a concentration of 0.1 vol %, instead of the above surfactant (comparison).

On the 21st day after the application, the state of growth of the plants was visually observed (growth inhibition rate (%)=0 (the same as the untreated plot) to 100 (complete kill)), and the results as shown in Tables b1 and b2 were obtained.

TABLE b1

| Compound No. 1 | Surfactant (tradename) | Growth inhibition rate (%) of crabgrass |
|---|---|---|
| The present invention | NIKKOL DDP-8 | 73 |
| | PLYSURF A219B | 60 |
| | ADECA COL PS-440E | 70 |
| Comparison | CITOWETT | 50 |

TABLE b2

| Compound No. 1 | Surfactant (tradename) | Growth inhibition rate (%) of velvetleaf |
|---|---|---|
| The present invention | NIKKOL DDP-8 | 93 |
| | PLYSURF A219B | 90 |
| | ADECA COL PS-440E | 93 |
| Comparison | CITOWETT | 73 |

Test Example 2

The results as shown in Tables b3 and b4 were obtained in the same manner as the above Test Example 1 except that a prescribed amount (15 g a.i./ha) of a water-based suspension concentrate comprising compound No. 53 as an active ingredient, prepared in accordance with the above Example 2, was used.

TABLE b3

| Compound No. 53 | Surfactant (tradename) | Growth inhibition rate (%) of crabgrass |
|---|---|---|
| The present invention | NIKKOL DDP-8 | 90 |
| | PLYSURF A219B | 78 |
| | ADECA COL PS-440E | 90 |
| Comparison | CITOWETT | 50 |

TABLE b4

| Compound No. 53 | Surfactant (tradename) | Growth inhibition rate (%) of velvetleaf |
|---|---|---|
| The present invention | NIKKOL DDP-8 | 98 |
| | PLYSURF A219B | 90 |
| | ADECA COL PS-440E | 93 |
| Comparison | CITOWETT | 78 |

Test Example 3

Upland field soil was put into a 1/1,000,000 ha pot, and seeds of crabgrass were sown and grown in a greenhouse. When crabgrass reached 4.5 to 5.0 leaf stage, a prescribed amount (30 g a.i./ha) of a water-based suspension concentrate comprising compound No. 238 as an active ingredient, prepared in accordance with the above Example 6, was diluted with water corresponding to 300 L/ha (containing 0.05 vol % of a surfactant containing the POA alkyl ether phosphate), followed by foliar application. Further, for comparison, foliar application was carried out in the same manner by using CITOWETT (tradename) at a concentration of 0.3 vol %, instead of the above surfactant.

On the 21st day after the application, the state of growth of the plant was evaluated in the same manner as in Test Example 1, and the results as shown in Table b5 were obtained.

TABLE b5

| Compound No. 238 | Surfactant (tradename) | Growth inhibition rate (%) of crabgrass |
|---|---|---|
| The present invention | NIKKOL DDP-8 | 90 |
| | NIKKOL TDP-8 | 90 |
| | PLYSURF A219B | 90 |
| | PHOSPHANOL RS710 | 80 |
| | ADEKA COL PS-440E | 75 |
| Comparison | CITOWETT | 50 |

Test Example 4

The results as shown in Tables b6 and b7 were obtained in the same manner as in the above Test Example 1 except that a prescribed amount (15 g a.i./ha or 7 g a.i./ha) of a wettable powder comprising compound No. 2-27 as an active ingredient, prepared in accordance with the above Example 4, was used.

TABLE b6

| Compound No. 2-27 (15 g a.i./ha) | Surfactant (tradename) | Growth inhibition rate (%) of crabgrass |
|---|---|---|
| The present invention | NIKKOL DDP-8 | 90 |
|  | PLYSURF A219B | 94 |
|  | ADECA COL PS-440E | 90 |
| Comparison | CITOWETT | 78 |

TABLE b7

| Compound No. 2-27 (7 g a.i./ha) | Surfactant (tradename) | Growth inhibition rate (%) of velvetleaf |
|---|---|---|
| The present invention | NIKKOL DDP-8 | 95 |
|  | PLYSURF A219B | 70 |
|  | ADECA COL PS-440E | 80 |
| Comparison | CITOWETT | 63 |

Test Example 5

The results as shown in Table b8 were obtained in the same manner as in the above Test Example 3 except that a prescribed amount (60 g a.i./ha) of a wettable powder comprising compound No. 3-31 as an active ingredient, prepared in accordance with the above Example 5, was used.

TABLE b8

| Compound No. 3-31 | Surfactant (tradename) | Growth inhibition rate (%) of crabgrass |
|---|---|---|
| The present invention | NIKKOL DDP-8 | 80 |
| Comparison | CITOWETT | 20 |

Test Example 6

Upland field soil was put into a 1/1,000,000 ha pot, and seeds of crabgrass were sown and grown in a greenhouse. When crabgrass reached 3.8 to 4.1 leaf stage, a prescribed amount (7 g a.i./ha) of a water-based suspension concentrate comprising compound No. 238 as an active ingredient, prepared in accordance with the above Example 3, was diluted with water corresponding to 300 L/ha (containing 0.03 vol % of a surfactant containing the POA alkyl ether phosphate and optionally having 0.03 vol % of a fatty acid ester, a hydrocarbon solvent or an emulsifying agent added), followed by foliar application. The fatty acid ester used here was AGNIQUE Me 18RD-F (tradename), the hydrocarbon solvent was Solvesso 150 (tradename) and the emulsifying agent was a mixture of a polyoxyethylene sorbitol tetraoleate, a polyoxyethylene castor oil and calcium dodecylbenzene sulfonate.

On the 20th day after the application, the state of growth of the plant was evaluated in the same manner as in Test Example 1, and the results as shown in Table b9 were obtained.

TABLE b9

| Compound No. 238 | Surfactant (tradename) | Fatty acid ester | Hydrocarbon solvent | Emulsifying agent | Growth inhibition rate (%) of crabgrass |
|---|---|---|---|---|---|
| The present invention | ADEKA COL PS-440E | — | — | — | 73 |
|  |  | added | — | added | 83 |
|  |  | — | added | added | 83 |
|  |  | added | added | added | 85 |

Test Example 7

Upland field soil was put into a 1/1,000,000 ha pot, and seeds of crabgrass were sown and grown in a greenhouse. When crabgrass reached 4.0 to 5.0 leaf stage, a prescribed amount (15 g a.i./ha) of a wettable powder comprising compound No. 2-1 as an active ingredient, prepared in accordance with the above Example 1, was diluted with water corresponding to 300 L/ha (containing 0.05 vol % of a surfactant containing the POA alkyl ether phosphate), followed by foliar application. Further, for comparison, foliar application was carried out in the same manner by using a silicon surfactant (tradename: SILWETT L-77) at a concentration of 0.1 vol % instead of the above surfactant.

On the 21st day after the application, the state of growth of the plant was evaluated in the same manner as in Test Example 1, and the results as shown in Table b10 were obtained.

TABLE b10

| Compound No. 2-1 | Surfactant (tradename) | Growth inhibition rate (%) of crabgrass |
|---|---|---|
| The present invention | Phosphanol RS-710 | 75 |
|  | PLYSURF A219B | 70 |
| Comparison | SILWETT L-77 | 10 |

Test Example 8

Upland field soil was put into a 1/1,000,000 ha pot, and seeds of barnyardgrass (*Echinochloa crus-galli* L) and crabgrass were respectively sown and grown in a greenhouse. When barnyardgrass reached 4.0 to 4.5 leaf stage and crabgrass reached 4.0 to 5.0 leaf stage, a prescribed amount (15 g a.i./ha) of a wettable powder comprising compound No. 2-6 as an active ingredient, prepared in accordance with the above Example 1, was diluted with water corresponding to 300 L/ha (containing 0.05 vol % of a surfactant containing the POA alkyl ether phosphate), followed by foliar application. Further, for comparison, foliar application was carried out in the same manner by using SILWETT L-77 (tradename.) at a concentration of 0.1 vol % instead of the above surfactant.

On the 21st day after the application, the state of growth of the plants was evaluated in the same manner as in Test Example 1, and the results as shown in Tables b11 and b12 were obtained.

TABLE b11

| Compound No. 2-6 | Surfactant (tradename) | Growth inhibition rate (%) of barnyardgrass |
|---|---|---|
| The present invention | PHOSPHOLAN PS-236 | 95 |
| Comparison | SILWETT L-77 | 10 |

TABLE b12

| Compound No. 2-6 | Surfactant (tradename) | Growth inhibition rate (%) of crabgrass |
| --- | --- | --- |
| The present invention | ADECA COL PS-440E | 75 |
| | NIKKOL DDP-8 | 70 |
| | NIKKOL TDP-8 | 73 |
| | PHOSPHANOL ML-240 | 85 |
| | PHOSPHANOL RS-710 | 70 |
| | PLYSURF A219B | 78 |
| Comparison | SILWETT L-77 | 40 |

Test Example 9

Upland field soil was put into a 1/1,000,000 ha pot, and seeds of crabgrass were sown and grown in a greenhouse. When crabgrass reached 4.0 to 4.5 leaf stage, a prescribed amount (15 g a.i./ha) of a wettable powder comprising compound No. 2-39 as an active ingredient, prepared in accordance with the above Example 1, was diluted with water corresponding to 300 L/ha (containing 0.05 vol % of a surfactant containing the POA alkyl ether phosphate), followed by foliar application. Further, for comparison, foliar application was carried out in the same manner by using SILWETT L-77 at a concentration of 0.1 vol % instead of the above surfactant.

On the 21st day after the application, the state of growth of the plant was evaluated in the same manner as in Test Example 1, and the results as shown in Table b13 were obtained.

TABLE b13

| Compound No. 2-39 | Surfactant (tradename) | Growth inhibition rate (%) of crabgrass |
| --- | --- | --- |
| The present invention | PHOSPHANOL RS-410 | 70 |
| | ADECA COL PS-440E | 93 |
| | NIKKOL DDP-8 | 93 |
| Comparison | SILWETT L-77 | 20 |

Test Example 10

The results as shown in Tables b14 and b15 were obtained in the same manner as in the above Test Example 8 except that a prescribed amount (15 g a.i./ha) of a wettable powder comprising compound No. 2-185 as an active ingredient, prepared in accordance with the above Example 1, was used.

TABLE b14

| Compound No. 2-185 | Surfactant (tradename) | Growth inhibition rate (%) of barnyardgrass |
| --- | --- | --- |
| The present invention | PHOSPHOLAN PS-236 | 80 |
| Comparison | SILWETT L-77 | 0 |

TABLE b15

| Compound No. 2-185 | Surfactant (tradename) | Growth inhibition rate (%) of crabgrass |
| --- | --- | --- |
| The present invention | NIKKOL DDP-8 | 70 |
| | NIKKOL TDP-8 | 70 |
| | PHOSPHANOL ML-240 | 70 |
| | PHOSPHANOL RS-710 | 73 |
| | PLYSURF A219B | 70 |
| Comparison | SILWETT L-77 | 20 |

Test Example 11

Upland field soil was put into a 1/1,000,000 ha pot, and seeds of crabgrass were sown and grown in a greenhouse. When crabgrass reached 4.0 to 5.0 leaf stage, a prescribed amount (15 g a.i./ha) of a wettable powder comprising compound No. 4-3 as an active ingredient, prepared in accordance with the above Example 1, was diluted with water corresponding to 300 L/ha (containing 0.05 vol % of a surfactant containing the POA alkyl ether phosphate), followed by foliar application. Further, for comparison, foliar application was carried out in the same manner by using SILWETT L-77 (tradename) at a concentration of 0.1 vol % instead of the above surfactant.

On the 21st day after the application, the state of growth of the plant was evaluated in the same manner as in Test Example 1, and the results as shown in Table b16 were obtained.

TABLE b16

| Compound No. 4-3 | Surfactant (tradename) | Growth inhibition rate (%) of crabgrass |
| --- | --- | --- |
| The present invention | PHOSPHANOL RS-410 | 80 |
| | ADECA COL PS-440E | 83 |
| | Phospholan PS-236 | 80 |
| | NIKKOL DDP-8 | 80 |
| | NIKKOL TDP-8 | 85 |
| | PHOSPHANOL ML-240 | 90 |
| | PHOSPHANOL RS-710 | 80 |
| | PLYSURF A219B | 98 |
| Comparison | SILWETT L-77 | 55 |

Test Example 12

The results as shown in Tables b17 were obtained in the same manner as in the above Test Example 11 except that a prescribed amount (15 g a.i./ha) of a wettable powder comprising compound No. 4-320 as an active ingredient, prepared in accordance with the above Example 1, was used.

TABLE b17

| Compound No. 4-320 | Surfactant (tradename) | Growth inhibition rate (%) of crabgrass |
| --- | --- | --- |
| The present invention | PHOSPHOLAN PS-236 | 90 |
| | NIKKOL DDP-8 | 90 |
| Comparison | SILWETT L-77 | 88 |

Test Example 13

Upland field soil was put into a 1/1,000,000 ha pot, and seeds of barnyardgrass were sown and grown in a greenhouse. When barnyardgrass reached 4.0 to 4.5 leaf stage, a prescribed amount (31 g a.i./ha) of a wettable powder comprising compound No. 5-1 as an active ingredient, prepared in accordance with the above Example 1, was diluted with water corresponding to 300 L/ha (containing 0.05 vol % of a surfactant containing the POA alkyl ether phosphate), followed by foliar application. Further, for comparison, foliar application was carried out in the same manner by using SILWETT L-77 (tradename) at a concentration of 0.1 vol % instead of the above surfactant.

On the 21st day after the application, the state of growth of the plant was evaluated in the same manner as in Test Example 1, and the results as shown in Table b18 were obtained.

TABLE b18

| Compound No. 5-1 | Surfactant (tradename) | Growth inhibition rate (%) of barnyardgrass |
|---|---|---|
| The present invention | ADECA COL PS-440E | 85 |
| Comparison | SILWETT L-77 | 70 |

INDUSTRIAL APPLICABILITY

By using the herbicidal composition of the present invention capable of improving the effect of a herbicidally active ingredient, it is possible to reduce the dose of the herbicide and thus substantially reduce the environmental load on a site where the herbicide is applied or the periphery thereof, and further, it is possible to substantially reduce the costs required for its transportation or storage. Thus, its applicability is very high irrespective of whether the application is to agricultural fields or non-agricultural fields.

The entire disclosure of Japanese Patent Application No. 2007-184482 filed on Jul. 13, 2007 including specification, claims, drawings and summary is incorporated herein by reference in its entirety.

The invention claimed is:

1. A herbicidal composition comprising (1) a compound represented by the formula (I) or its salt:

(I)

wherein T is $T^1$:

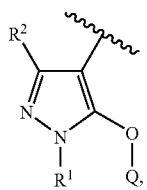

$T^2$:

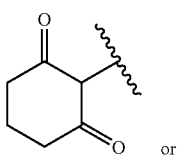

or $T^3$:

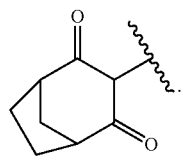

and Z is $Z^1$:

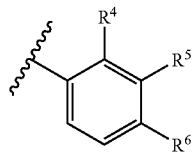

or $Z^2$:

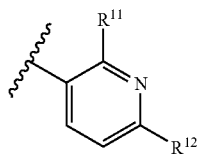

Q is —C(O)SR$^3$, hydrogen or -A-O—C(O)OR$^{10}$, R$^1$ is alkyl, R$^2$ is hydrogen or alkyl, R$^3$ is alkyl; or haloalkyl; R$^4$ is alkyl; haloalkyl; or halogen; R$^5$ is alkoxyalkyl; haloalkoxyalkyl; amino(thiocarbonyl)alkyl which may be substituted by at least one substituent selected from the group consisting of alkyl, cyano, cyanoalkyl, (alkylthio)carbonylalkyl, alkyl(thiocarbonyl)alkyl, —C(O)OR$^7$ and —C(O)SR$^7$; thiocyanatoalkyl; alkoxy; alkenyloxy; alkynyloxy; haloalkoxy; alkoxyalkoxy; haloalkoxyalkoxy; alkoxyhaloalkoxy; haloalkoxyhaloalkoxy; alkoxyalkoxyalkyl; alkylthio; alkoxyalkylthio; haloalkoxyalkylthio; alkoxyhaloalkylthio; haloalkoxyhaloalkylthio; alkylthioalkylthio; haloalkylthioalkylthio; alkylthiohaloalkylthio; haloalkylthiohaloalkylthio; alkylthioalkoxy; —OC(O)OR$^7$; —C(O)OR$^7$; —C(O)SR$^7$; —C(S)OR$^7$; or —C(S)SR$^7$;

R$^6$ is alkylsulfinyl; or alkylsulfonyl,

R$^7$ is or haloalkyl;

R$^{10}$ is alkyl, A is alkylene substituted by at least one alkyl,

R$^{11}$ is alkoxyalkoxyalkyl, and

R$^{12}$ is haloalkyl, provided that when T is T$^1$ or then, Z is Z$^1$, when T is then, Z is Z$^2$, then in addition when T is T$^1$ and R$^5$ is hydrogen then, Q is not hydrogen, and when T is then, R$^5$ is not hydrogen, and (2) a polyoxyalkylene alkyl ether phosphate or its salt.

2. The herbicidal composition according to claim 1, wherein in the formula (I), T is T$^1$, Q is hydrogen, R$^1$ is alkyl, R$^2$ is hydrogen, Z is Z$^1$, R$^4$ is alkyl, R$^5$ is alkoxyalkyl, alkoxy, alkoxyalkoxy or —C(O)OR$^7$, and R$^6$ is alkylsulfonyl.

3. The herbicidal composition according to claim 2, wherein in the formula (I), T is T$^1$, Q is hydrogen, R$^1$ is alkyl, R$^2$ is hydrogen, Z is Z$^1$, R$^4$ is alkyl, R$^5$ is alkoxyalkoxy, and R$^6$ is alkylsulfonyl.

4. The herbicidal composition according to claim 1, wherein in the formula (I), T is T$^1$, Q is -A-O—C(O)OR$^{10}$, R$^1$ is alkyl, R$^2$ is hydrogen, Z is Z$^1$, R$^4$ is alkyl, R$^5$ is alkoxyalkyl, alkoxy, alkoxyalkoxy or —C(O)OR$^7$, R$^6$ is alkylsulfonyl, A is alkylene substituted by at least one alkyl, and R$^{10}$ is alkyl.

5. The herbicidal composition according to claim 4, wherein in the formula (I), T is T$^1$, Q is -A-O—C(O)OR$^{10}$, R$^1$ is alkyl, R$^2$ is hydrogen, Z is Z$^1$, R$^4$ is alkyl, R$^5$ is alkoxyalkoxy, R$^6$ is alkylsulfonyl, A is alkylene substituted by at least one alkyl, and R$^{10}$ is alkyl.

6. The herbicidal composition according to claim 1, wherein in the formula (I), T is T$^2$, Z is Z$^1$, R$^4$ is halogen, R$^5$ is haloalkoxyalkyl, and R$^6$ is alkylsulfonyl.

7. The herbicidal composition according to claim 1, wherein in the formula (I), T is T$^3$, Z is Z$^2$, R$^{11}$ is alkoxyalkoxyalkyl, and R$^{12}$ is haloalkyl.

8. The herbicidal composition according to claim 1, which further contains (3) at least one oil selected from the group consisting of a vegetable oil, a fatty acid ester and a hydrocarbon solvent.

9. The herbicidal composition according to claim 1, which further contains (3) at least one oil selected from the group consisting of a vegetable oil, a fatty acid ester and a hydrocarbon solvent, and (4) an emulsifying agent.

10. A method for improving the herbicidal effect of (1) the compound represented by the formula (I) or its salt as defined in claim 1, by mixing (2) a polyoxyalkylene alkyl ether phosphate or its salt with the compound represented by the formula (I).

11. The method according to claim 10, wherein (3) at least one oil selected from the group consisting of a vegetable oil, a fatty acid ester and a hydrocarbon solvent, is further mixed.

12. The method according to claim 10, wherein (3) at least one oil selected from the group consisting of a vegetable oil, a fatty acid ester and a hydrocarbon solvent, and (4) an emulsifying agent, are further mixed.

13. A method for controlling undesired plants, which comprises applying a herbicidally effective amount of the herbicidal composition as defined in claim 1, to the undesired plants or to a place where they grow.

14. A method for controlling undesired plants, which comprises applying (1) the compound represented by the formula (I) or its salt as defined in claim 1, and (2) a polyoxyalkylene alkyl ether phosphate or its salt, to the undesired plants or to a place where they grow.

\* \* \* \* \*

UNITED STATES PATENT AND TRADEMARK OFFICE
CERTIFICATE OF CORRECTION

PATENT NO. : 8,435,928 B2
APPLICATION NO. : 12/668725
DATED : May 7, 2013
INVENTOR(S) : Hiroshi Kikugawa et al.

It is certified that error appears in the above-identified patent and that said Letters Patent is hereby corrected as shown below:

In the Claims

Column 48, line 39, "when T is $T^1$ then, Z is $Z^1$," should read
--when T is $T^1$ or $T^2$ then Z is $Z^1$,-- line 40, "when T is then Z is $Z^2$, then addition" should read
--when T is $T^3$ then Z is $Z^2$, then in addition--;

line 43, "when T is then, $R^5$ is not hydrogen, and (2) a polyoxyalky-"
should read --when T is $T^2$ then $R^5$ is not hydrogen, and (2) a
polyoxyalky- --.

Signed and Sealed this
Seventeenth Day of September, 2013

Teresa Stanek Rea
*Deputy Director of the United States Patent and Trademark Office*

UNITED STATES PATENT AND TRADEMARK OFFICE
CERTIFICATE OF CORRECTION

Page 1 of 2

PATENT NO. : 8,435,928 B2
APPLICATION NO. : 12/668725
DATED : May 7, 2013
INVENTOR(S) : Hiroshi Kikugawa et al.

It is certified that error appears in the above-identified patent and that said Letters Patent is hereby corrected as shown below:

In the Specification

Column 5, line 43, "NIKKOL TCP-4" should read --NIKKOL TLP-4--.

Column 10, lines 12-13, "propisochloror dimeth-achlor" should read
--propisoclor or dimethaclor--.

Column 20, TABLE a2-continued, line 61,
"2-7   Et   H   $SO_2Me$   $CO_2Me$   $SO_2Me$" should read
--2-7   Et   H   $SO_2Me$   $CO_2Me$   $SO_2Me$ CN--.

Column 25, line 20, No. 3-83, "$SC_2CH_2SCH_3$" should read --$SC_2CH_2SCF_3$--;

21, No. 3-84, "$SC_2CH_2SCH_3$" should read --$SC_2CH_2SCF_3$--;

22, No. 3-85, "$SC_2CH_2SCH_3$" should read --$SC_2CH_2SCF_3$--;

23, No. 3-86, "$SC_2CH_2SCH_3$" should read --$SC_2CH_2SCF_3$--;

24, No. 3-87, "$SC_2CH_2SCH_3$" should read --$SC_2CH_2SCF_3$--.

In the Claims

Column 48, line 39, "when T is $T^1$ or then, Z is $Z^1$," should read
--when T is $T^1$ or $T^2$ then Z is $Z^1$,--;

This certificate supersedes the Certificate of Correction issued September 17, 2013.

Signed and Sealed this
Eighth Day of October, 2013

Teresa Stanek Rea
*Deputy Director of the United States Patent and Trademark Office* line 40, "when T is then, Z is $Z^2$, then addition" should read
--when T is $T^3$ then Z is $Z^2$--;

line 41, "hydrogen then," should read --hydrogen then--;

line 43, "when T is then, $R^5$ is not hydrogen, and (2) a polyoxyalky-" should read --when T is $T^2$ then $R^5$ is not hydrogen, and (2) a polyoxyalky- --.

Column 48, line 35, "$R^7$ is or haloalkyl;" should read --$R^7$ is alkyo or haloalkyl--.

UNITED STATES PATENT AND TRADEMARK OFFICE
CERTIFICATE OF CORRECTION

PATENT NO. : 8,435,928 B2
APPLICATION NO. : 12/668725
DATED : May 7, 2013
INVENTOR(S) : Hiroshi Kikugawa et al.

It is certified that error appears in the above-identified patent and that said Letters Patent is hereby corrected as shown below:

In the Specification
Column 5, line 43, "NIKKOL TCP-4" should read --NIKKOL TLP-4--.

Column 10, lines 12-13, "propisochloror dimeth-achlor" should read
--propisoclor or dimethaclor--.

Column 20, TABLE a2-continued, line 61,
"2-7  Et  H  $SO_2Me$  $CO_2Me$  $SO_2Me$" should read
--2-7  Et  H  $SO_2Me$  $CO_2Me$  CN--.

Column 25, line 20, No. 3-83, "$SC_2CH_2SCH_3$" should read --$SC_2CH_2SCF_3$--;
line 21, No. 3-84, "$SC_2CH_2SCH_3$" should read --$SC_2CH_2SCF_3$--;
line 22, No. 3-85, "$SC_2CH_2SCH_3$" should read --$SC_2CH_2SCF_3$--;
line 23, No. 3-86, "$SC_2CH_2SCH_3$" should read --$SC_2CH_2SCF_3$--;
line 24, No. 3-87, "$SC_2CH_2SCH_3$" should read --$SC_2CH_2SCF_3$--.

In the Claims
Column 48, line 39, "when T is $T^1$ or then, Z is $Z^1$," should read
--when T is $T^1$ or $T^2$ then Z is $Z^1$,--;

This certificate supersedes the Certificates of Correction issued September 17, 2013 and October 8, 2013.

Signed and Sealed this
Thirty-first Day of December, 2013

Margaret A. Focarino
*Commissioner for Patents of the United States Patent and Trademark Office* line 40, "when T is then, Z is $Z^2$, then addition" should read --when T is $T^3$ then Z is $Z^2$--;

line 41, "hydrogen then," should read --hydrogen then--;

line 43, "when T is then, $R^5$ is not hydrogen, and (2) a polyoxyalky-" should read --when T is $T^2$ then $R^5$ is not hydrogen, and (2) a polyoxyalky- --.

Column 48, line 35, "$R^7$ is or haloalkyl;" should read --$R^7$ is alkyl or haloalkyl--.